(12) United States Patent
Mozes et al.

(10) Patent No.: US 6,613,536 B1
(45) Date of Patent: Sep. 2, 2003

(54) SYNTHETIC PEPTIDES AND PHARMACEUTICAL COMPOSITIONS COMPRISING THEM FOR THE TREATMENT OF SYSTEMIC LUPUS ERYTHEMATOSUS

(75) Inventors: Edna Mozes, Rehovot (IL); Ari Waisman, Tel-Aviv (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 08/913,994

(22) PCT Filed: Mar. 27, 1996

(86) PCT No.: PCT/US96/04206
§ 371 (c)(1),
(2), (4) Date: Sep. 29, 1997

(87) PCT Pub. No.: WO96/30057
PCT Pub. Date: Oct. 3, 1996

(30) Foreign Application Priority Data

Mar. 28, 1995 (IL) .................................................. 113159

(51) Int. Cl.⁷ ........................ A61K 38/00; C07K 14/00; C07K 16/00
(52) U.S. Cl. ...................... 435/7.24; 530/300; 530/326; 530/350; 435/7.1; 435/7.5; 424/185.1
(58) Field of Search ................................ 530/300, 371, 530/350; 424/185.1; 435/7.1, 7.24, 7.5

(56) References Cited

FOREIGN PATENT DOCUMENTS

WO          9630057 A1  *  10/1996

OTHER PUBLICATIONS

Tisch, R and McDevitt HO. Proc. Nat. Acad. Sci. (USA). 91–437–438. Jan. 1994.*
Mannik, M et al. in "Harrison's Principles of Internal Medicine; 10th ed.". ed. by Petersdorf et al. McGraw–Hill, New York. p. 387.*
The Merck Manual of Dianosis and Therapy: 16th ed. ed by Bondy et al. Merck Research Laboratories, Rahway, NJ. pp. 1316–1321. 1992.*
Waisman, A. et al., PNAS 94(9): 4620–25, Modulation of murine systemic lupus erythematosus with peptides based on complementarity determining regions of a pethogenic anti–DNA monoclonal antibody. (abstract), 1997.*
A. Waisman et al., "Modulation of Murine Systemic Lupus Erythematosus With Peptides Based on Complementarity Determining Regions of a Pathogenic Anti–DNA Monoclonal Antibody", Proc. Natl. Acad. Sci. USA, vol. 94, p. 4620–4625, Apr., 1997.

H. Fricke et al., "Induction of Experimental Systemic Lupus Erythematosus in Mice by Immunization With a Monoclonal Anti–La Autoantibody", International Immunology, vol. 2, No. 3, p. 225–230, 1990.
S. Mendlovic et al., "Induction of a Systemic Lupus Erythematosus–Like Disease in Mice by a Common Human Anti–DNA Idiotype", Proc. Natl. Acad. Sci. USA, vol. 85, p. 2260–2264, Apr., 1988.
S. Mendlovic et al., "The Role of Anti–Idiotypic Antibodies in the Induction of Experimental Systemic Lupus Erythematosus in Mice", Eur. J. Immunol., vol. 19, p. 729–734, 1989.
P.J. Ruiz et al., "Induction of Experimental Systemic Lupus Erythematosus in Mice by Immunization With the F(ab')₂ Fragment of the Human Anti–DNA Monoclonal Antibody Carrying the 16/6 Idiotype", Immunology Letters, vol. 41, p. 79–84, 1994.
Waisman, Ari et al., "The role of the 16/6 idiotype network in the induction and manifestations of systemic lupus erythematosus.", International Immunology, vol. 5, No. 10, pp. 1293–1300.
Sthoeger, Zev M. et al., "Monoclonal anticardiolipin antibodies derived from mice with experimental lupus erythematosus:characterization and the induction of a secondary antiphospholipid syndrome.", J. of Clin. Immun., vol. 13, No. 2, pp. 127–138 (1993).
Fricke, H. et al., "Idiotype specific T–cell lines inducing experimental systemic lupus erythematosus in mice.", Immunology, vol. 73, pp. 421–427 (1991).
Mendlovic, S. et al., "The genetic regulation of the induction of experimental SLE.", Immunology, vol. 69, pp. 228–236 (1990).
Waisman, Ari et al., "Variable region sequences of autoantibodies from mice with experimental systemic lupus erythematosus.", Eur. J. Immunol., vol. 23, pp. 1566–1573 (1993).

* cited by examiner

*Primary Examiner*—Gerald R. Ewoldt
(74) *Attorney, Agent, or Firm*—Browdy and Neimark, P.L.L.C.

(57) ABSTRACT

Synthetic peptides based on a complementarity-determining region (CDR) of the heavy or light chain of a pathogenic anti-DNA monoclonal antibody that induces a systemic lupus erythematosus (SLE)-like disease in mice, and analogs, and salts and chemical derivatives thereof; dual peptides comprising two such peptides or analogs covalently linked to one another either directly or through a short linking chain; peptide polymers comprising a plurality of sequences of said peptide or analog thereof; and peptide polymers attached to a macromolecular carrier, are disclosed, and pharmaceutical compositions comprising them for the treatment of SLE in humans.

28 Claims, 10 Drawing Sheets

—□— mAb 5G12
—◇— pep Iα
—○— pep IIIα
—△— p278
—⊞— NORMAL

——□—— mAb 5G12
······◇······ pep Ia
---○--- pep IIIa
---△--- p278
---⊞--- NORMAL ■ NON-IMMUNIZED
▦ pep Ia
☰ pep IIIa
▨ p278

- ■ — Tol' pep Ia, inj pep Ia
- □ — Tol' pep Ia, inj mAb 5G12
- ● — Tol' p307, inj pep Ia
- ▲ — Tol' p307, inj mAb 5G12

▫ pep Ia - SLE
◇ pep IIa - SLE
○ pep IIIa - SLE
△ 5G12 - SLE
▨ p195-212-SLE
◆ pep Ia - HEALTHY
⊕ pep IIa - HEALTHY
▽ pep IIIa - HEALTHY
▰ 5G12 - HEALTHY
⬥ p195-212-HEALTHY

SYNTHETIC PEPTIDES AND PHARMACEUTICAL COMPOSITIONS COMPRISING THEM FOR THE TREATMENT OF SYSTEMIC LUPUS ERYTHEMATOSUS

This application is a 371 national stage application of PCT/US96/04206, filed Mar. 27, 1996, which claims the benefit of priority to Israel Application No. 113,159, filed Mar. 28, 1995.

FIELD OF THE INVENTION

The present invention relates to synthetic peptides and to pharmaceutical compositions comprising them useful for the treatment of systemic lupus erythematosus (SLE) in humans.

BACKGROUND OF THE INVENTION

Autoimmune diseases are characterized by immune responses that are directed against self antigens. These responses are maintained by the persistent activation of self-reactive T lymphocytes. T lymphocytes are specifically activated upon recognition of foreign and/or self antigens as a complex with self major histocompatibility complex (MHC) gene pro(ducts on the surface of antigen-presenting cells (APC).

Systemic lupus erythematosus (SLE) is an autoimmune disease of unknown origin and cure. Despite the extensive research on the mechanisms underlying the induction and development of SLE, the information available on the etiology of the disease is very limited due to the heterogeneity of SLE patients on one hand, and the lack of an experimental model in which the induction of the disease could be controlled, on the other hand.

The cause of SLE is unknown and it has heterogeneous clinical manifestations. Furthermore, no specific treatment aimed towards the prevention or cure of SLE is available. Despite the extensive research on the mechanisms underlying the induction of SLE, the information on the etiology of the disease is very limited. Studies on SLE have been performed until recently using peripheral blood lymphocytes (PBL) of patients at different clinical stages and under various treatment protocols. Alternatively, murine strains that develop spontaneous SLE-like disease were investigated as a model for SLE. This kind of analysis led to incomplete and confusing interpretations of the role of various immunological and non-immunological factors in either inducing or sustaining the disease, mainly due to the heterogeneity of patients on one hand and the inability to control the induction phase of the disease in murine SLE strains on the other hand.

Several years ago, an animal model of SLE has been established in the laboratory of one of the present inventors. This model, based on the concept of the idiotypic network, developed a wide spectrum of lupus-related autoantibodies and clinical manifestations (Mendlovic et al., 1988). The induction was carried out by the immunization of mouse strains that do not develop any spontaneous autoimmune disorders, with a human anti-DNA monoclonal antibody (mAb) which bears a common idiotype termed 16/6 Id (Shoenfeld et al., 1983). Following immunization, the mice produced antibodies specific to the 16/6 Id, antibodies that bear the 16/6 Id and antibodies directed against different nuclear antigens (dsDNA, ssDNA, Sm, ribonucleoprotein (RNP), Ro, La and others). The serological findings were associated with leukopenia, elevated erythrocyte sedimentation rate, proteinuria, abundance of immune complexes in the kidneys and sclerosis of the glomeruli (Mendlovic et al., 1988), which are typical manifestations of SLE. The present inventors have further shown that the experimental disease could be induced by a murine anti-16/6 Id mAb (Mendlovic et al., 1989) and by the mouse anti-anti 16/6 Id (16/6 Id+) mAb (Waisman et al., 1993). The induction of the disease is genetically controlled, and thus is strain dependent (Mendlovic et al., 1990). This unique model for the induction of experimental SLE provides the appropriate tools to clearly dissect the different steps and the linked immune parameters involved in the induction and development of SLE.

SLE is a systemic autoimmune disease characterized by the formation of autoantibodies against self-antigens, such as DNA, Sm, Ro, La, RNP, cardiolipin and histones. The etiology of SLE is unknown, and understanding the mechanism by which these self-antibodies arise might provide insight to this problem. For this purpose, the present inventors have produced a variety of monoclonal autoantibodies derived from C3H.SW mice in which experimental SLE was induced. As a rule, the monoclonal autoantibodies that were capable of eliciting antibodies that bear the 16/6 Id or react with it were found to be pathogenic and thus capable of inducing experimental SLE (Fricke et al., 1990; Sthoeger et al., 1993). Later on, the variable (V) regions of nine autoantibodies-that bind either DNA or HeLa nuclear extract (NE), isolated from the C3H.SW mice with experimental SLE, were sequenced (Waisman and Mozes, 1993). Monoclonal antibodies with different specificity were analyzed in an attempt to determine the connections between the different autoantibodies. Three mAb were found to bind DNA, and were shown to exhibit sequence characteristics of pathogenic anti-DNA antibodies. One of these mAb, designated 2C4C2, was shown to use a heavy (H) chain V region gene ($V_H$) identical to the $V_H$ of anti-DNA mAb isolated from other lupus-prone mice, namely (NZB×NZW)$F_1$. The light (L) chain V region gene ($V_L$) of mAb 2C4C2 is 98% homologous to the $V_L$ of another anti-DNA mAb, also isolated from (NZB×NZW)$F_1$ mice. The other two anti-DNA mAb, designated 5G12-4 and 5G12-6, share 93% of their $V_H$ sequences with that of mAb 2C4C2. Six mAb bound proteins of HeLa NE. The nine mAb use a total of five $V_H$ and four $V_L$ germ-line genes, demonstrating that the autoantibodies induced in mice with experimental SLE do not originate from one B cell clone. Three of the nine $V_H$ and $V_L$ were identical in sequence to germ-line genes, while at least three others had somatic mutations. The latter suggests that these autoantibodies arise in mice by both usage of existing (pre-immune) B cells, and through an antigen-driven process. Furthermore, it appears that autoantibodies found in mice with experimental SLE use genetic elements similar to those used by mAb that were isolated from mouse strains which develop lupus spontaneously.

T cells play an important role in the induction and development of experimental SLE. Thus, T cell lines and clones specific to the 16/6 Id were shown to induce experimental SLE in syngeneic recipients similarly to the 16/6 antibody. Therefore, following the inoculation of the activated cells of the lines, the mice developed both the serology and the renal damage which is typical to SLE (Fricke et al., 1991). Furthermore, a 16/6 Id specific T cell line of C3H.SW origin induced SLE in C57BL/6 mice that were shown to be resistant to the induction of the disease following injections with either the 16/6 Id or the anti-16/6 Id mAb (Mendlovic et al., 1990).

In an attempt to identify the pathogenic region of the 16/6 Id, (Fab')$_2$ fragments were prepared of the 16/6 Id mAb and were found to retain the specificity and pathogenic capacity of the whole 16/6 Id molecule (Ruiz et al., 1994).

The mAb 5G12 that was isolated from mice with experimental SLE and was shown to bind DNA and bear the 16/6 Id, is capable of inducing experimental SLE in mice (Waisman et al., 1993). T cells that react specifically to mAb by proliferation, are probably reacting to peptides representing sequences from their complementarity-determining regions (CDR). It is very likely that the T cells recognize the V regions of the above antibodies since they do not react with other antibodies that carry the same constant region but have different specificities. Within the variable region, the regions with the highest probability to be recognized are the CDR, since those are the regions that differ the most between the various antibodies. The CDR regions of the $V_H$ sequences of the nine pathogenic murine mAb mentioned above that induce SLE in mice, are boxed in FIG. 1 of Waisman and Mozes, 1993, in which the complete nucleotide and deduced amino acid sequences for the $V_H$ of the nine mAb are presented.

SUMMARY OF THE INVENTION

It is an object of the present invention to provide means for specific treatment of patients with SLE.

For this purpose, the invention provides peptides and analogs thereof based on the CDR regions of pathogenic monoclonal autoantibodies isolated from mice with experimental SLE.

Thus, in one aspect, the invention relates to a synthetic peptide selected from the group consisting of:
  (i) a peptide of at least 12 and at most 30 amino acid residues based on a complementarity-determining region (CDR) of the heavy or light chain of a pathogenic anti-DNA monoclonal antibody that induces a systemic lupus erythematosus (SLE)-like disease in mice (hereinafter CDR-based peptide), a salt or a chemical derivative thereof,
  (ii) an analog of a CDR-based peptide defined in (i), a salt or a chemical derivative thereof;
  (iii) a dual synthetic peptide comprising two such peptides of (i) or analogs of (ii) covalently linked to one another either directly or through a short linking chain;
  (iv) a peptide polymer comprising a plurality of sequences of said peptide (i) or analog thereof (ii); and
  (v) a peptide polymer (iv) attached to a macromolecular carrier.

In one embodiment of this aspect, the synthetic peptide is capable of:
  (i) inhibiting specifically the proliferative response and cytokine secretion of T lymphocytes of mice that are high responders to SLE-inducing autoantibodies; or
  (ii) inhibiting development of SLE in mice that are susceptible to SLE-induction by pathogenic autoantibodies.

The synthetic peptides and analogs thereof according to the invention may be selected from the group consisting of peptides having the sequences I to V herein, wherein:
  (i) the peptide of sequence I has the formula:
    T G Y Y $X_1$ $X_2$ $X_3$ $X_4$ $X_5$ Q S P E K S L E W I G (SEQ ID NO:1) [I]
      wherein $X_1$ is Met, Ala or Val; $X_2$ is Gln, Asp, Glu or Arg; $X_3$ is Trp or Ala; $X_4$ is Val or Ser; and $X_5$ is Lys, Glu or Ala;
  (ii) the peptide of sequence II has the formula:
    E I N P S T G G $X_6$ $X_7$ $X_8$ $X_9$ $X_{10}$ $X_{11}$ $X_{12}$ K A K A T (SEQ ID NO:2) [II]
      wherein $X_6$ and $X_7$ are each Thr, Val or Ala; $X_8$ is Tyr or Phe; $X_9$ is Asn or Asp; $X_{10}$ is Gln or Glu; $X_{11}$ is Lys or Glu, and $X_{12}$ is Phe or Tyr;
  (iii) the peptide of sequence III has the formula:
    Y Y C A R $X_{13}$$X_{14}$ $X_{15}$ $X_{16}$ P Y A $X_{17}$ $X_{18}$ Y W G Q G S (SEQ ID NO:3) [III]
      wherein $X_{13}$ is Phe, Thr or Gly; $X_{14}$ is Leu, Ala or Ser; $X_{15}$ is Trp or Ala; $X_{16}$ is Glu or Lys; $X_{17}$ is Met or Ala, and $X_{18}$ is Asp, Lys or Ser;
  (iv) the peptide of sequence IV has the formula:
    G Y N $X_{19}$ $X_{20}$ $X_{21}$ $X_{22}$ $X_{23}$ $X_{24}$ S H G $X_{25}$ $X_{26}$ L E W I G (SEQ ID NO:4) [IV]
      wherein $X_{19}$ is Met or Ala; $X_{20}$ is Asn, Asp or Arg; $X_{21}$ is Trp or Ala; $X_{22}$ is Val or Ser; $X_{23}$ is Lys or Glu; $X_{24}$ is Gln or Ala; $X_{25}$ is Lys or Glu, and $X_{26}$ is Ser or Ala; and
  (v) the peptide of sequence V has the formula:
    Y Y C A R $X_{27}$ $X_{28}$ $X_{29}$ Y G $X_{30}$ $X_{31}$ $X_{32}$ G Q G T L (SEQ ID NO:5) [V]
  wherein $X_{27}$ is Ser or Phe; $X_{28}$ is Gly or Ala; $X_{29}$ is Arg, Ala or Glu; $X_{30}$ is Asn or Asp; $X_{31}$ is Tyr or Phe, and $X_{32}$ is Trp, His or Ala.

In preferred embodiments, peptides I to V have the sequences Ia–Va herein:

T G Y Y M Q W V K Q S P E K S L E W I G (SEQ ID NO:6) (Ia)

E I N P S T G G T T Y N Q K F K A K A T (SEQ ID NO:7) (IIa)

Y Y Y C A R F L W E P Y A M D Y W G Q G S (SEQ ID NO:8) (IIIa)

G Y N M N W V K Q S H G K S L E W I G (SEQ ID NO:9) (IVa)

Y Y C A R S G R Y G N Y W G Q G T L (SEQ ID NO:10) (Va)

Peptides Ia to IIIa are based on the CDR1, CDR2 and CDR3 regions, respectively, of the $V_H$ chain of mAb 5G12, and peptides IVa and Va are based on the CDR1 and CDR3 regions, respectively, of the $V_H$ chain of mAb 2C4C2 (Waisman and Mozes, 1993).

In another aspect, the invention relates to pharmaceutical compositions for the treatment of SLE comprising a synthetic peptide or peptide polymer of the invention and a pharmaceutically acceptable carrier.

In still another aspect, the invention relates to a method of treatment of a SLE patient comprising administering to a SLE patient an effective amount of a synthetic peptide or peptide polymer of the invention.

DETAILED DESCRIPTION OF THE INVENTION

Figure 1A:
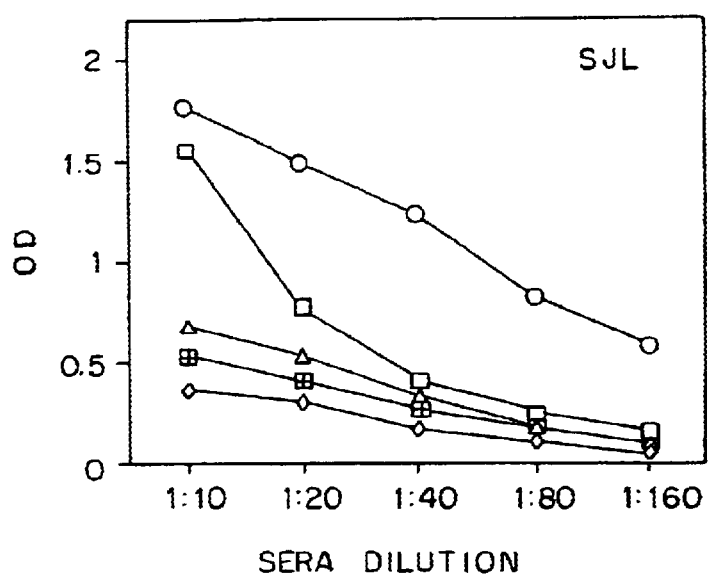
FIGS. 1A–B show the presence of anti-DNA antibodies in sera of SJL (1A) and BALB/c (1B) mice immunized with mAb 5G12, peptides Ia and IIIa and a control peptide 278, or non-immunized. Sera of individual SJL or BALB/c mice immunized with either one of the indicated antigens, taken three months after the booster injection, and sera of age-matched naive mice, were tested for anti-ssDNA antibody titers. Following incubation with the diluted sera, goat anti-mouse IgG (γ-chain specific) conjugated to peroxidase was added. Results were expressed as mean OD of each mouse group.

The present invention relates to synthetic peptides that are based on the CDR of monoclonal pathogenic autoantibodies isolated from mice with experimental SLE. Such monoclonal antibodies are obtained from supernatants of hybridomas produced by fusion, for example, of spleen cells of C3H.SW mice immunized with an anti-16/6 Id mAb, with X63.653 plasmacytoma cells (Waisman and Mozes, 1993).

Examples of such peptides are those of formulas Ia to Va herein, based on, respectively, the CDR1, CDR2 and CDR3 regions of the heavy chain of mAb 5G12 and the CDR1 and CDR3 regions of the heavy chain of mAb 2C4C2 (Waisman and Mozes, 1993), and analogs thereof.

Analogs of parent peptides Ia–Va contemplated by the invention include substitution, deletion and addition analogs as described herein. Substitution analogs have amino acid substitutions at different positions, these substitutions being made based on the volume, hydrophobic-hydrophilic pattern and charge of the amino acids.

Amino acids may be divided along the lines of volume, hydrophobic-hydrophilic pattern and charge. With respect to volume, those of ordinary skill in the art understand that the amino acids with the largest volume are Trp, Tyr, Phe, Arg, Lys, Ile, Leu, Met and His, while those with the smallest volumes are Gly, Ala, Ser, Asp, Thr and Pro, with others being in between.

With respect to hydrophobic-hydrophilic pattern, it is well known that the amino acids Gly, Ala, Phe, Val, Leu, Ile, Pro, Met and Trp are hydrophobic, whereas all of the remaining amino acids are hydrophilic. Among the hydrophilic amino acids, Ser, Thr, Gln, and Tyr have no charge, while Arg, Lys, His and Asn have a positive charge and Asp and Glu have negative charges.

In selecting peptides to be tested for their potential in inhibiting the proliferative response of T lymphocytes of mice that are high responders to SLE-inducing autoantibodies, it is important that the substitutions be selected from those which cumulatively do not substantially change the volume, hydrophobic-hydrophilic pattern and charge of the corresponding portion of the unsubstituted parent peptide. Thus, a hydrophobic residue may be substituted with a hydrophilic residue, or vice-versa, as long as the total effect does not substantially change the volume, hydrophobic-hydrophilic pattern and charge of the corresponding unsubstituted parent peptide.

It should be understood that other modifications of the peptides and analogs thereof are also contemplated by the present invention. Thus, the peptide or analog of the present invention is intended to include a "chemical derivative" thereof which retains at least a portion of the function of the peptide which permits its utility in preventing or inhibiting T cell proliferative responses and autoimmune disease.

A "chemical derivative" of a peptide or analog of the present invention contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues. Many such chemical derivatives and methods for making them are well known in the art.

Also included in the scope of the invention are salts of the peptides and analogs of the invention. As used herein, the term "salts" refers to both salts of carboxyl groups and to acid addition salts of amino groups of the peptide molecule. Salts of a carboxyl group may be formed by means known in the art and include inorganic salts, for example, sodium, calcium, ammonium, ferric or zinc salts, and the like, and salts with organic bases such as those formed for example, with amines, such as triethanolamine, arginine, or lysine, piperidine, procaine, and the like. Acid addition salts include, for example, salts with mineral acids such as, for example, hydrochloric acid or sulfuric acid, and salts with organic acids, such as, for example, acetic acid or oxalic acid. Such chemical derivatives and salts are preferably used to modify the pharmaceutical properties of the peptide insofar as stability, solubility, etc., are concerned.

Examples of peptides and analogs thereof are as follows:
(i) Peptide Ia of the Formula:
1 2 3 4 5 6 7 8 9 10 11 12 13 14 15 16 17 18 19 20 T G Y Y M Q W V K Q S P E K S L E W I G (SEQ ID NO:6)
(Ia)

and substitution analogs thereof in which Met at position 5 is substituted by either Ala or Val; Gln at position 6 is substituted by either Asp, Glu or Arg; Trp at position 7 is substituted by Ala; Val at position 8 by Ser; and Lys at position 9 is substituted by either Glu or Ala; and deletion analogs thereof in which up to 5 amino acid residues are deleted from the C-terminal of peptide Ia.

(ii) Peptide IIa of the Formula:
1 2 3 4 5 6 7 8 9 10 11 12 13 14 15 16 17 18 19 20 E I N P S T G G T T Y N Q K F K A K A T (SEQ ID NO:7)
(IIa)

and substitution analogs thereof in which Thr in positions 9 and 10 are each substituted by either Val or Ala; Tyr at position 11 is substituted by Phe; Asn at position 12 is substituted by Asp; Gln at position 13 by Glu; Lys at position 14 by Glu; and Phe at position 15 by Tyr, and deletion analogs thereof in which up to 5 amino acid residues are deleted from the C-terminal of peptide IIa.

(iii) Peptide IIIa of the Formula:
1 2 3 4 5 6 7 8 9 10 11 12 13 14 15 16 17 18 19 20 Y Y C A R F L W E P Y A A M D Y W G Q G S (SEQ ID NO:8) (IIIa)

and substitution analogs thereof in which Phe at position 6 is substituted by either Thr or Gly; Leu at position 7 is substituted by either Ala or Ser; Trp at position 8 is substituted by Ala; Glu at position 9 is substituted by Lys; Met at position 13 by Ala; and Asp at position 14 by either Lys or Ser; and deletion analogs thereof in which up to 5 amino acid residues are deleted from the C-terminal of peptide IIIa.

(iv) Peptide IVa of the Formula:

1 2 3 4 5 6 7 8 9 10 11 12 13 14 15 16 17 18 19 G Y N M N W V K Q S H G K S L E W I G (SEQ ID NO:9) (IVa)

and substitution analogs thereof in which Met at position 4 is substituted by Ala; Asn at position 5 is substituted by either Asp or Arg; Trp at position 6 is substituted by Ala; Val at position 7 by Ser; Lys at position 8 by Glu; Gin at position 9 by Ala; Lys at position 13 by Glu; and Ser at position 14 by Ala; and deletion analogs thereof in which up to 5 amino acid residues are deleted from the C-terminal of peptide IVa.

(v) Peptide Va of the Formula:

1 2 3 4 5 6 7 8 9 10 11 12 13 14 15 16 17 18 Y Y C A R S G R Y G N Y W G Q G T L (SEQ ID NO:10) (V)

and substitution analogs thereof in which Ser at position 6 is substituted by Phe; Gly at position 7 is substituted by Ala; Arg at position 8 is substituted by either Ala or Glu; Asn at position 1 is substituted by Asp; Tyr at position 12 by Phe; and Trp at position 13 by either His or Ala; and deletion analogs thereof in which up to 5 amino acid residues are deleted from the C-terminal of peptide Va.

Once an analog in accordance with the present invention is produced, its ability to inhibit the proliferative response of T lymphocytes of mice that are high responders to SLE-inducing autoantibodies may be readily determined by those of ordinary skill in the art without undue experimentation using tests such as those described herein. One test which may be readily conducted is for the ability of substituted peptides to inhibit in vitro the proliferative responses of certain T cell lines and clones specific to SLE-inducing autoantibodies. The T cell lines and clones may, for example, be the T cell lines and clones specific to the 16/6 Id mAb (Fricke et al., 1991) established from immunized lymph node cells of mice by previously described methodology (Axelrod and Mozes, 1986). Cells are exposed to the stimulating antibody presented on irradiated syngeneic spleen cells in the presence of enriched medium every two weeks. The T cell lines are cloned by the standard limiting dilution technique.The proliferative responses of these T cell lines and clones are tested, for example, by the method described in Materials and Methods, section (g), herein.

Another test which can be conducted in order to select analogs having the desired activity is to test for the ability of the substituted peptides to inhibit the ability of the T cell lines and clones to provide help to peptide-specific B cells in the presence of the parent peptide. The substituted peptides may also be tested for their ability to bind directly, following biotinylation, to MHC Class II products on antigen-presenting cells of the relevant strains. For this purpose, N-terminal biotinylation of the relevant peptides is performed at 0° C. with an excess of biotin-N-hydroxysuccinimide in aqueous solution (Mozes et al., 1989). Mouse splenic adherent cells or human peripheral blood lymphocyte (PBL)-adherent cells ($1\times10^6$/sample) are incubated with biotinylated peptides in PBS containing 0.1% bovine serum albumin (PBS/BSA) at 37° C. for 20 hr, followed by incubation with phycoerythrin-streptavidin for 30 min at 4° C. After each incubation, the cells are washed twice with the above solution. Thereafter, the cells are analyzed by flow cytometry using FACScan. In each analysis, a minimum of 5000 cells are examined (for above procedures, see, for example, Mozes et al., 1989; Zisman et al., 1991).

A further test which can be conducted is to test for the ability of the analogs to inhibit cytokine secretion by the T cell line or by T lymphocytes oh lymph nodes of mice that are high responders to SLE-inducing autoantibodies. The cytokines are detected as follows: IL-1 activity is assessed either by ELISA using a pair of capture and detecting antibodies (as described below for IL-4, IL-6, IL-10) or using the LBRM-33(1A5) assay (Conlon, 1983) in which 1A5 cells are stimulated in the presence of phytohemagglutinin (PHA), with either supernatants or recombinant IL-1 at various concentrations to secrete IL-2. Following an overnight incubation, supernatants of 1A5 cells are transferred to the IL-2 dependent cytotoxic T lymphocyte (CTLL) line. Stimulation of the CTLL line by IL-2 is measured after 24 hr by incorporation of $^3$[H]-thymidine. IL-2 is directly detected using the IL-2 dependent CTLL line or by ELISA. Levels of IL-4, IL-6, IL-10, INFγ and TNFα in the supernatants are determined by ELISA using antibodies to the various cytokines (Phamingen, San Diego, Calif., USA) according to the manufacturer's instructions.

Peptides which test positive in one or more of these in vitro tests will provide a reasonable expectation of in vivo activity. However, in vivo tests can also be conducted without undue experimentation. Thus, for example, adult mice may be injected with the candidate peptide at either day −3 or day 0. The mice are then immunized with the disease-inducing autoantibody or with the peptide. Ten days later, lymph node cells of the mice are tested for their ability to proliferate to the immunogen in order to find out the inhibitory capacity of the candidate peptide.

Another it7 vivo animal test consists in measuring the therapeutic activity directly in the murine model in7 vivo for the production of SLE as described above. The peptides can be injected into the mice in which experimental SLE is induced by different routes at different dosages and at different time schedules. In order to determine the pharmacokinetic parameters of the analogs, including volume of distribution, uptake into antigen-presenting cells and clearance, one can use biotinylated derivatives of the analogs. The concentration of the soluble fraction of the analogs in the various body fluids can be determined by ELISA, using avidin-coated plates and specific anti-peptide antibodies. Cell bound analogs can be analyzed by FACS, using fluorochromo-conjugated avidin or streptavidin. Furthermore, the treated mice can be tested periodically in order to determine the effect of the peptides on the autoantibody responses and on disease manifestations elicited in the mice by the SLE-inducing autoantibody.

Another in vivo procedure consists in tolerizing newborn mice with the candidate peptide followed by immunization of the mice with the pathogenic autoantibody, such as 16/6 Id+, or with the same peptide, and following the disease manifestations, such as serological findings associated with leukopenia, elevated erythrocyte sedimentation rate, proteinuria, abundance of immune complexes in the kidneys and sclerosis of the glomeruli.

It can thus be seen that, besides the preferred embodiments which have been shown to be operable in the examples herein, those of ordinary skill in the art will be able to determine additional analogs which will also be operable following the guidelines presented herein without undue experimentation.

A relatively simple iii vitro test can also be conducted in order to assay for the expected therapeutic efficacy of any given substituted peptide on any given SLE patient. In order to assess the ultimate goal of producing peptides that will bind with high affinity to the appropriate MHC Class II molecules but will not lead to further activation of T cells and will therefore have a therapeutic effect on SLE patients, the peptides may be assayed, following biotinylation, for their ability to bind directly to HLA Class II products on antigen-presenting cells in the peripheral blood lymphocytes of the SLE patients. Healthy control donors and control peptides may be used in such assays to verify their specificity.

A preferred form of the therapeutic agent of the invention is a peptide selected from the group of peptides of formulas I to V herein, including peptides Ia to Va and substitution and/or deletion analogs thereof.

Another preferred form of the therapeutic agent in accordance with the present invention is the form of a multiepitope single peptide. Thus, in a preferred embodiment, dual petides consisting of two different peptides selected from the group of peptides of formula I–V herein, are covalently linked to one another, such as by a short stretch of alanine residues or by a putative site for proteolysis by cathepsin. See, for example, U.S. Pat. No. 5,126,249 and European Patent 495,049 with respect to such sites. This will induce site-specific proteolysis of the preferred form into the two desired analogs. Alternatively, a number of the same or different peptides of the present invention may be formed into a peptide polymer, such as, for example, polymerization of the peptides with a suitable polymerization agent, such as 0.1% glutaraldehyde (Audibert et al. (1981), *Nature* 289:593). The polymer will preferably contain from 5 to 20 peptide residues. Such peptide polymers may also be formed by crosslinking the peptides or attaching multiple peptides to macromolecular carriers. Suitable macromolecular carriers are, for example, proteins, such as tetanus toxoid, and linear or branched copolymers of amino acids, such as a linear copolymer of L-alanine, L-glutamic acid and L-lysine and a branched copolymer of L-tyrosine, L-glutamic acid, L-alanine and L-lysine (T,G)-A-L-, or multichain poly-DL-alanine (M. Sela et al. 1955, *J. Am. Chem. Soc.* 77:6175). The conjugates are obtained, for example, by first coupling the peptide with a water-soluble carbodiimide, such as 1-ethyl-3-(3'-dimethylaminopropyl)carbodiimide hydrochloride, and then performing the conjugation with the macromolecular carrier as described by Muller, G. M. et al. (1982) Proc. Natl. Acad. Sci. USA 79:569. The contents of the coupled peptide in each conjugate are determined by amino acid analysis, in comparison to the composition of the carrier alone.

According to one embodiment of the present invention, one or more active peptides may be attached to a suitable macromolecular carrier or may be polymerized in the presence of glutaraldehyde.

The peptides, polymers thereof or their conjugates with suitable macromolecular carriers, will be given to patients in a form that insures their bioavailability, making them suitable for treatment. If more than one peptide analog is found to have significant inhibitory activity, these analogs will be given to patients in a formulation containing a mixture of the peptides.

The invention further includes pharmaceutical compositions comprising at least one synthetic peptide according to the invention, a conjugate thereof with a suitable macromolecular carrier or a polymer thereof optionally with a pharmaceutically acceptable carrier.

Any suitable route of administration is encompassed by the invention, including oral, intravenous, subcutaneous, intraarticular, intramuscular, inhalation, intranasal, intrathecal, intraperitoneal, intradermal, transdermal or other known routes, including the enteral route.

The dose ranges for the administration of the compositions of the present invention should be large enough to produce the desired effect, whereby, for example, an immune response to the SLE-inducing autoantibody, as measured by T cell proliferation in vitro, is substantially prevented or inhibited, and further, where the disease is significantly treated. The doses should not be so large as to cause adverse side effects, such as unwanted cross reactions, generalized immunosuppression, anaphylactic reactions and the like.

Effective doses of the peptides of this invention for use in treating SLE are in the range of about 1 $\mu$g to 100 mg/kg body weight. The dosage administered will be dependent upon the age, sex, health, and weight of the recipient, kind of concurrent treatment, if any, frequency of treatment, and the nature of the effect desired.

The synthetic peptides and analogs of the invention, particularly those of sequences I to V herein, are aimed at inhibiting or suppressing specific antigen responses of SLE patients, without affecting all other immune responses. This approach is of the utmost importance since most diagnosed patients are young women that have to be treated for many years and the currently accepted treatment for SLE involves administration of immuno-suppressive agents, such as corticosteroids and/or cytotoxic drugs, that are both non-specific and have multiple adverse side effects.

The present invention will now be described in more detail in the following non-limiting Examples and the accompanying figures:

EXAMPLES

Materials and Methods a) Mice:

Mice (BALB/c and SJL/J) were obtained from the Jackson Laboratory, Bar Harbor, Me., USA and from Olac, Show's farm, Bicesper Oxon, England. Mice were used at the age of 6–12 weeks. In some studies neonatal mice were also used.

b) Human mAb 16/6 Id:

The human mAb 16/6 is an anti-DNA antibody originally of the IgM isotype and switched in culture to IgGl. The mAb was derived from a patient and expresses a common idiotype, the 16/6 Id (Shoenfeld et al., 1983; Mendlovic et al., 1988). The hybridoma cells secreting this mAb are routinely grown in culture, and the antibody is isolated from culture supernatants using an affinity column of Protein G coupled to Sepharose™.

c) Production of Mouse mAb 5G12 and 2C4C2:

Experimental SLE was induced in C3H.SW female mice by immunization with the previously described murine anti-16/6 Id mAb (Mendlovic et al., 1989). Four months later, two mice were sacrificed and their spleen cells were fused with X63.653 plasmacytoma cells. Hybridoma cells that secreted autoantibodies were cloned by limiting dilution in 96-well microtiter plates. The sequence characteristics of nine monoclonal autoantibodies secreted by nine of the hybridoma clones were characterized (Waisman and Mozes, 1993). The mAb designated 5G12 and 2C4C2 were isolated and affinity purified from the hybridoma supernatants using a goat anti-mouse Ig-Sepharose™ 4B column. The 5G12 mAb was found to be an anti-DNA mAb that bear the 16/6 Id and have the IG2a isotype. The 2C4C2 mAb was found to be an anti-DNA and anti-cardiolipin mAb and to be of the IgM isotype. The nucleotide and deduced amino acid sequences for the $V_H$ of both 5G12 and 2C4C2 mAb are presented in FIG. 1 of Waisman and Mozes, 1993, in which figure the CDR regions are boxed.

d) Induction of Experimental SLE in Mice:

Mice were injected with the human monoclonal 16/6 Id (1 µg/mouse) or the murine 16/6 Id mAb, e.g. mAb 5G12 (20 µg/mouse), in complete Freund's adjuvant in the hind footpads. Three weeks following injection, the mice were boosted with the same amount of the immunizing antibody in phosphate-buffered saline (PBS).The mice were then tested for autoantibody production and clinical manifestations characteristic of experimental SLE.

e) Detection of SLE-associated Clinical Manifestations:

The erythrocyte sedimentation rate was determined by diluting the heparinized blood in PBS at a ratio of 1:1. The diluted blood was then passed to a microsampling pipette and the sedimentation was measured 6 hours later. White blood cell counts were determined after the hemolysis of heparinized blood. Proteinuria was measured in a semi-quantitative manner, using a Combistix kit (Ames, Stoke Poges, Slough, U.K.). Immunohistology was performed by incubation of fixed frozen cryostat sections with FITC-labeled antibodies to mouse Ig. Staining was visualized via use of a fluorescent microscope.

f) Enzyme-linked Immunosorbent Assay (ELISA):

ELISA was utilized for the detection and quantitation of antibodies in experimental mice, and in humans. Polystyrene microtiter plates were coated with the relevant antigen or antibody, and sera dilutions or supernatants derived from the human or mouse cell cultures were added to the blocked plates. Specific binding was determined following the addition of peroxidase-conjugated antibodies against the appropriate immunoglobulin (Ig) (e.g. goat anti-human or goat anti-mouse peroxidase-conjugated antibodies) and the peroxidase substrate. Optical densities were read at 414 nm using an ELISA reader.

g) Proliferative Responses of Splenic and Lymph Node Cells:

Cells ($0.5 \times 10^6$/well) derived from the spleen and lymph nodes of treated and untreated mice were cultured in microtiter plates in the presence of different concentrations of the various immunizing pathogenic autoantibodies. At the end of 96 hours incubation, 0.5 µCi of $^3$H-thymidine was added for an additional 18 hours, after which cells were harvested and radioactivity was counted.

h) Treatment of Experimental Mice:

In order to either prevent induction of experimental SLE or to cure mice afflicted with the disease, the following procedures were used: (i) Newborn mice were tolerized with a peptide of the invention (100 µg of the peptide in PBS, intraperitoneally at 24 and 72 hours after birth). Six weeks later, the mice were immunized with the pathogenic autoantibody, e.g. 5G12 (16/6 Id+) and examined for disease manifestations; (ii) A first group of adult mice was injected with various concentrations of the peptides before disease induction with the pathogenic autoantibody or pathogenic T cell line; another group was injected with the peptides to be tested for their therapeutic effect six weeks following immunization at the peak of the serological response; and a further group was treated at 4–6 months post-immunization after the establishment of the overt SLE disease. The number of injections with the peptides was determined based on their effect on the disease induction and progression. The effect of the peptide treatment on T cell proliferation, on the autoantibody production and on the disease manifestations was then evaluated.

i) Proliferative Responses of T Cell Lines and Clones:

T cell lines and clones specific to the 16/6 Id were established from immunized lymph node cells as previously described (Axelrod and Mozes, 1986). Cells were exposed to the stimulating antibody presented on irradiated syngeneic spleen cells in the presence of enriched medium every two weeks. The T cell lines were cloned by the limiting dilution technique. Cells ($10^4$/well) were cultured with $0.5 \times 10^6$ irradiated (3000 rad) syngeneic spleen cells in the presence of different concentrations of either the specific stimulator of the line or control reagents. At the end of 48 hours incubation, 0.5 µCi of $^3$H-thymidine were added for an additional 18 hours, after which cells were harvested and radioactivity was counted.

j) Proliferation and Cytokine Production by Peripheral Blood Lymphocytes (PBL):

PBL from human SLE patients and of the appropriate control donors ($2 \times 10^5$/well) were cultured in microtiter plates in enriched medium containing 10% pooled AB sera in the presence of the human or mouse monoclonal 16/6 Id antibody, in the presence of peptides of the invention or in the presence of phytohemagglutinin (PHA). The rate of proliferation was evaluated by the incorporation of $^3$[H]-thymidine in the cell culture. Non-relevant peptides were used as specificity controls. Antigen and mitogen-stimulated cytokine production was quantitated in the supernatants of the above cultures using either the cytokine-dependent lines or the appropriate pairs of antibodies in ELISA assays. Inhibition of the proliferative responses was performed in vitro by adding increasing doses of the tested peptide analogs into the proliferative culture mixtures.

k) Human T Cell Lines and Clones:

Human T cell lines specific to the 16/6 Id may be established from PBL of either SLE patients or controls following stimulation in vitro with either the human or mouse mAb 16/6 Id or the peptides. The maintenance and cloning of the lines was performed similarly to that described above for the murine T cell lines, with the exception that the stimulation was performed using either autologous irradiated cells or EBV-transformed lines of autologous PBL (used as antigen-presenting cells).

l) Biotinylation of Peptides: N-terminal biotinylation of the peptides was performed in 0.1N sodium bicarbonate solution at room temperature, with excess of biotinamidocaproate N-hydroxysuccinimide ester (Sigma, St. Louis, Mo.) dissolved in 1-methyl-2-pyrrolidone (Sigma).

m) Direct Binding of Biotinylated Peptides to APC:

Spleen cells suspended in RPMI 1640 medium containing 10% FCS were incubated in Petri dishes for 60 min at 37° C. Thereafter, non-adherent cells were removed, the plates were washed, and the adherent cells were collected from the plates using a rubber policeman (Costar, Mass., USA). These cells ($1 \times 10^6$/100 µl/tube) were incubated with the biotinylated peptides in PBS containing 0.1% BSA (high purity grade, Amresco, Ohio, USA) for 16 hr at 37° C., followed by incubation with phycoerythrin (PE)-streptavidin (Jackson ImmunoResearch) for 30 min at 4° C. Thereafter the samples were incubated with biotinylated anti-streptavidin (1:60, Vector Laboratories, Burlingame, Calif.) and for an additional period with PE-streptavidin, all for 30 min at 4° C. The cells were washed twice with cold PBS/BSA solution after each incubation. Thereafter, cells were analyzed by flow cytometry using the FACSort cytometer and CELLQuest software (Beckton-Dickinson, Mountain View, Calif.). Three antibodies were used for inhibition of binding in these experiments: 34-5-3 (anti-I-A$^h$, Pharmingen, San Diego, Calif.); MKD6 (anti-I-A$^d$, Beckton-Dickinson) and 10.3.6.2 (anti-I-A$^s$ (Zamvil et al., 1988)).

Example 1
Synthesis of the Peptides

The synthetic peptides of the invention of the formulas Ia, IIa and IIIa herein as well as control peptides were prepared with an automated synthesizer (Applied Biosystem model 430A, Germany) using the manufacturer's protocols for t-butyloxycarbonyl (BOC) procedure (see Kent et al., 1984; Schnolzer et al., 1992). Briefly, in this procedure, commercially available side-chain protected amino acids were used, the amino acids being added at each step with at least 99% efficiency. The protecting groups were removed from the peptides and were cleared from the resin with anhydrous HF. Subsequently, the peptides were purified by extraction with ethyl acetate or isopropyl acetate and by HPLC. The purity of the peptides Ia, IIa and IIIa so obtained was then verified by HPLC and amino acid analysis.

For the preparation of peptides IVa and Va herein and analogs of the peptides Ia to Va of the invention, the same procedure as noted above may be used.

The peptides Ia, IIa and IIIa were then analyzed for their biological activity and other characteristics as set forth in Examples 2–14 below. It is to be understood that the other peptides not so-tested may be subjected to the same analysis.

Example 2
Detection of Anti-DNA Antibodies in the Sera of Mice Immunized With Peptides Ia and IIIa SJL/J and BALB/c female mice (6–8 week old) were immunized with 20 µg of peptide Ia or IIIa of the invention, or with a control peptide designated p278 (the peptide desinated Pep 278h described in published PCT International Application WO 94/03208) or with mAb 5G12 emulsified in complete Freund's adjuvant (CFA) in the foot pads. Three weeks later the mice received a booster injection with the same amount of peptide or mAb, in PBS. Thereafter, blood was drawn every two weeks. A fifth group included non-immunized mice.

FIG. 1 depicts the anti-DNA antibodies in the sera of mice three months after the booster injection, and is very similar to the amount of the autoantibodies produced in later periods.

As shown in FIG. 1A, SJL/J mice that were immunized with the peptide IIIa (open circles) show a high level of anti-DNA antibodies, that is higher than that of mice immunized with the whole antibody 5G12 (open boxes). Low levels of anti-DNA antibodies were observed in the sera of SJL/J mice immunized with either the peptide Ia (open diamonds), control peptide p278 (open triangles) or normal non-immunized mice (crossed square).

Figure 1B:
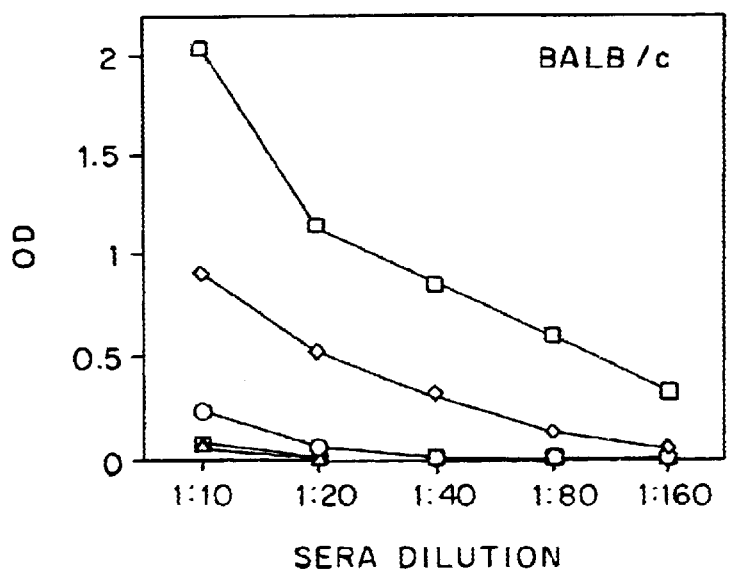

As shown in FIG. 1B, BALB/c mice that were immunized either with the whole antibody 5G12 (open boxes) or the peptide Ia (open diamonds) show presence of anti-DNA antibodies in the sera. However, sera of BALB/c mice immunized with either the peptide IIIa (open circles), p278 (open triangles) or normal non-immunized mice (crossed square) did not show presence of anti-DNA antibodies.

ELISA was utilized to test the presence of the anti-DNA antibodies in the sera of the mice, as follows : Plates (Nunc) were coated for 90 min with 10 µg/ml of methylated BSA. Thereafter the plates were washed (all the washes were 3 times with PBS/0.05% Tween 20 (Sigma)) and incubated for an additional 90 min with 10 µg/ml of single-stranded DNA (calf thymus DNA (Sigma) that was heated for 15 min at 90° C. and fast-cooled). The plates were washed and blocked overnight with 1% ovalbumin in PBS (Sigma). Thereafter, the plates were washed and incubated with the sera of the mice diluted in the blocking reagent, followed by wash and incubation with 1:500 dilution of goat anti-mouse IgG (Fc receptor specific) polyclonal antibody conjugated to peroxidase. The plates were then washed and developed using ABTS substrate (Sigma), and the color was read using an ELISA reader at 414 nm. Results are expressed as mean OD of each mouse group (5 mice per group).

Example 3
Detection of Anti-nuclear Extract (NE) Antibodies in the Sera of Mice Immunized With the Peptides Ia and IIIa Five groups of mice were immunized according to Example 2, and their sera were tested for the presence of anti-NE antibodies.

Figure 2A:
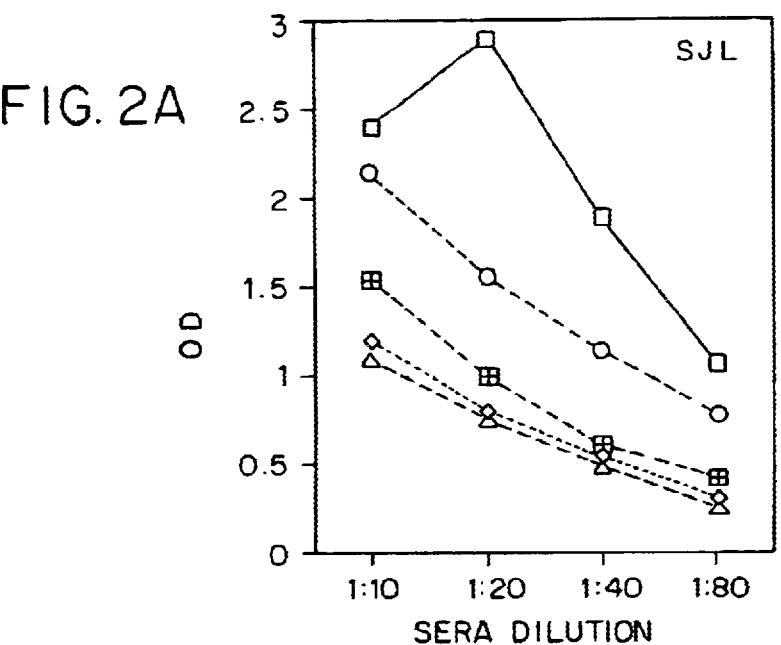
FIGS. 2A–B show the presence of HeLa anti-nuclear extract (NE) antibodies in the sera of SJL (2A) and BALB/c (2B) mice immunized with same antigens as in FIG. 1.

As shown in FIG. 2A, SJL/J mice immunized with the mAb 5G12 (open squares) or with the peptide IIIa (open circles) produced a high level of anti-NE antibodies, whereas mice immunized with the peptide Ia (open diamonds) or p278 control peptide (open triangles), or normal non-immunized mice (crossed squares), produced lower levels of anti-NE antibodies.

Figure 2B:
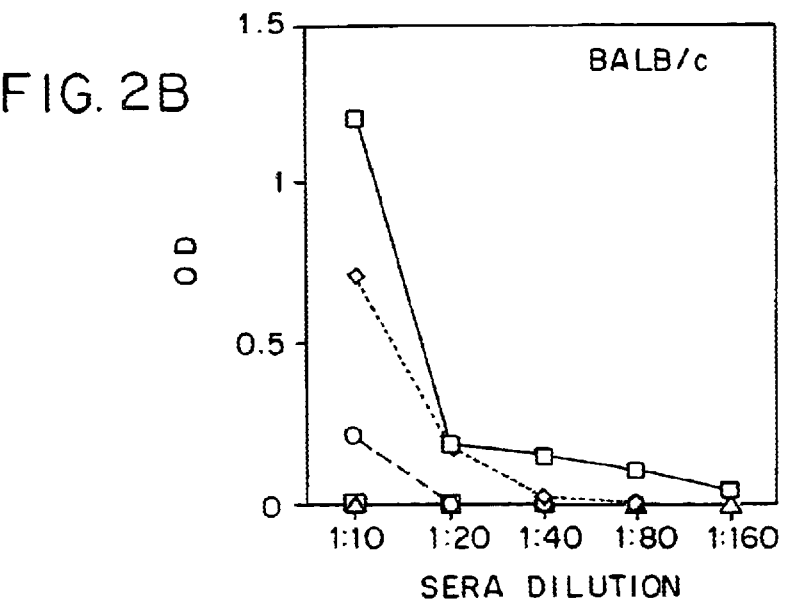

As shown in FIG. 2B, BALB/c mice immunized with the mAb 5G12 (open squares) or with the peptide Ia (open diamonds) produced high levels of anti-NE antibodies, whereas very low level of anti-NE antibodies was detected in the sera of BALB/c mice immunized with the peptide IIIa (open circles). No anti-NE antibodies were detected in the group of mice immunized with p278 control peptide (open triangles) or in normal non-immunized mice (crossed squares).

ELISA was utilized to test the presence of the anti-NE antibodies in the sera of the mice, as follows: Plates (Nunc) were coated with 5 µg/ml of of HeLa cells NE for 90 min. Thereafter plates were washed and blocked, and ELISA was continued the next day, as described in Example 2 for anti-DNA antibodies.

Example 4
Detection of Anti-RNP, Sm, Ro and La Antibodies in the Sera of Mice Immunized With the Peptides Ia and IIIa The same sera of the mice as described in Examples 2 and 3 were used for detection of anti-RNP, Sm, Ro and La antibodies.

Figure 3A:
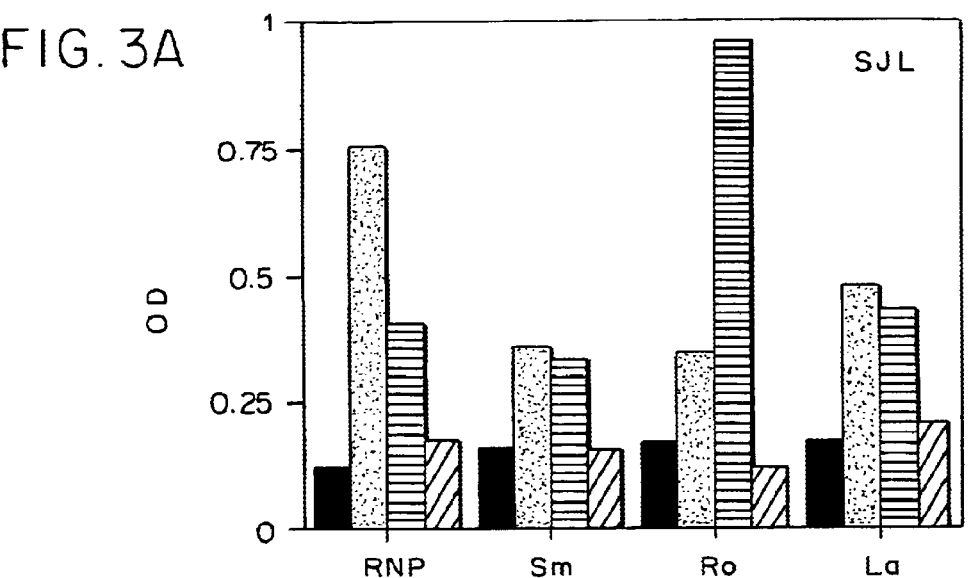
FIGS. 3A–B show the presence of anti-RNP, Sm, Ro and La antibodies in the sera of SJL (3A) and BALB/c (3B) mice immunized with peptides Ia and IIIa or with control peptide 278, and normal mice.

As shown in FIG. 3A, SJL/J mice immunized with the peptide IIIa (lined box) produced extremely high levels of anti-Ro autoantibodies, antibodies that are typical for SLE in humans. High levels of anti-RNP, anti-Sm and anti-La antibodies were detected not only in SJL/J mice immunized with the peptide IIIa (lined box), but also with the peptide Ia (closed box), as compared to normal mice (open box) or to mice immunized with the control peptide p278 (dotted box).

Figure 3B:
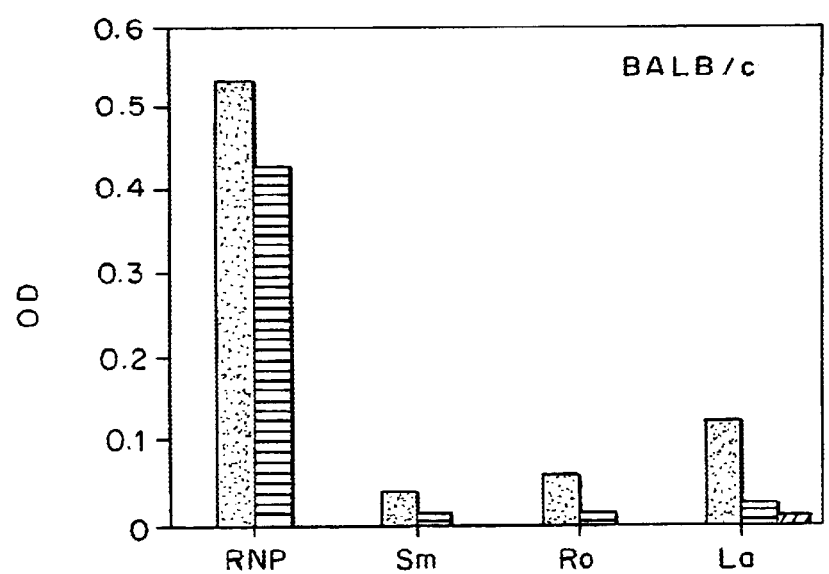

As shown in FIG. 3B, BALB/c mice immunized with the peptide Ia (closed box) or the peptide IIIa (lined box) produced very high levels of anti-RNP antibodies. However, BALB/c mice immunized with the peptide IIIa (lined box) showed very low levels of anti-Sm, anti-La and anti-Ro antibodies, as compared to BALB/c mice immunized with the peptide Ia (closed box) which produced detectable antibodies in the sera.

Plates were purchased as pre-coated plates and were blocked with 1% ovalbumin in PBS for 2 hr. Thereafter the plates were washed as in Example 2 above, incubated in duplicates with 1:10 diluted sera, washed again and ELISA was carried out as described in Example 2 above.

Example 5
Clinical Manifestations of SLE in Mice Immunized With the Peptides Ia and IIIa BALBtc and SJL mice were immunized with mAb 5G12 or with peptides Ia and IIIa, and five months later were checked by two criteria for manifestation of SLE: white blood cell count (WBC) and proteinuria.

(i) White blood cell count (WBC): The mice were bled, their blood was diluted 1:10 with 1% (vol/vol) acetic acid in order to eliminate the red blood cells, and white blood cells were counted under a normal light microscope.

Proteinuria: The urine of the mice was tested using combisticks (Combistix Kit, Ames) for the presence of protein. High levels of protein in the urine are indicative of kidney damage, a typical manifestation of SLE.

to the peptide IIIa but not to non-relevant control peptide p278, and upon stimulation with peptide IIIa, secreted the Th1-type cytokines, namely, IL-2, IFNγ and TNFα. Injection of the T cell line into syngeneic healthy mice led to the production of autoantibodies and development of clinical manifestations that are characteristic to mice with experimental SLE. These results confirm the role of the CDR-based peptides of the invention in experimental SLE and demonstrate the role of the peptide-specific T cells in the autoimmune disease.

TABLE 1

Clinical manifestations of mice immunized with the peptides

| Immunization | BALB/c W.B.C.[a] | BALB/c proteinuria[b] | SJL W.B.C.[a] | SJL proteinuria[b] |
|---|---|---|---|---|
| mAb 5G12 | 3800 ± 400 | 0.975 ± 0.08 | Nd[c] | 0.81 ± 0.07 |
| pep Ia | 3375 ± 350 | 0.88 ± 0.076 | Nd[c] | 0.375 ± 0.04 |
| pep IIIa | 3325 ± 400 | 0.30 ± 0.01 | 3300 ± 1343 | 0.9 ± 0.075 |
| p278 | 6470 ± 920 | 0.33 ± 0.02 | 7150 ± 320 | 0.2 ± 0.25 |
| non-immunized | 6800 ± 1200 | 0.1 ± 0 | 8100 ± 475 | 0.5 ± 0 |

[a]W.B.C., white blood cell counts per mm$^3$
[b]proteinuria (g/l)
[c]ND, not done The results for both WBC and proteinuria are shown in Table 1: Mice immunized with either the mAb 5G12 or the peptides Ia or IIIa had a lower number of white blood cells in comparison to non-immunized mice or those immunized with p278 control peptide. High levels of protein were measured in the urine of both BALB/c and SJL mice immunized with mAb 5G12, of SJL mice immunized with the IIa peptide and of BALB/c mice immunized with the Ia peptide, while a smaller increase in protein level was detected in the urine of both mice immunized with control peptide p278, of IIa-immunized BALB/c mice anf of Ia-immunized SJL mice.

Example 6
Specificity of Mice Response to the Peptides

As shown in previous examples, the peptides Ia and IIa were used for the immunization of different mouse strains, in parallel to their immunization with the whole monoclonal antibody. The draining lymph nodes of the mice proliferated to the immunizing peptides to different extents, depending on the mouse strains. Thus, BALB/c mice were found to be high responders to peptide Ia, whereas SJL mice were found to be high responders to peptide IIIa. Both peptides were used in attempts to induce experimental SLE using the protocol utilized for the pathogenic autoantibodies. It was found that SJL mice that were immunized with peptide IIIa and BALB/c mice that were immunized with peptide Ia produced elevated levels of autoantibodies including anti-DNA (see FIG. 1) and anti-NE antibodies (see FIG. 2). Moreover, the immunized mice developed leukopenia and proteinuria (see Table 1) similarly to mice in which experimental SLE has been induced using the murine anti-DNA, 16/6 Id+ pathogenic 5G12 mAb. Kidney analysis of the peptide-injected mice revealed mild immune complex deposits in part of the mice. These results indicate that peptides Ia and IIIa are important T cell epitopes of the whole molecule of the pathogenic autoantibody.

In order to assess the correlation between the peptides of the invention and T cells, a T cell line specific to peptide IIIa of SJL origin (high responders to the peptide IIa) was established. The T cells of the line proliferated specifically Example 7
Detection of Anti-DNA and Anti-NE Antibodies in the Sera of BALB/c Mice Tolerized With the Peptide Ia and Immunized With Either Peptide Ia or mAb 5G12

In order to further elucidate the role of the peptides in SLE, peptide Ia was utilized for the induction of tolerance in BALB/c mice. Newborn mice were injected twice (at day 1 and 3) with either peptide Ia or a control peptide. Thus, neonatal BALB/c mice, 24 hr old, were injected intraperitoneally (i.p.) with 100 μg of the peptide Ia or the control peptide p307 (a peptide related to myasthenia gravis described in published PCT Application No. WO 94/00148) in PBS, and received a second injection 48 hr later with the same amount of peptide. Six to seven weeks after injection, the mice were immunized as described in Example 2 above with either the mAb 5G12 or the peptide Ia. The mice were bled two weeks after boost (and then periodically every two weeks) and the sera of the mice were tested for the presence of anti-DNA or anti-NE antibodies, as described in Examples 1 and 2 above. The assays performed to measure these autoantibody titers in the sera of the experimental mice indicated that the mice that were tolerized with peptide Ia did not produce significant titers of antibodies to either DNA or nuclear extract antigens, whereas mice tolerized to the control peptide p307 prior to their immunization with peptide Ia or the mAb 5G12 produced high autoantibody titers.

Figure 4A:
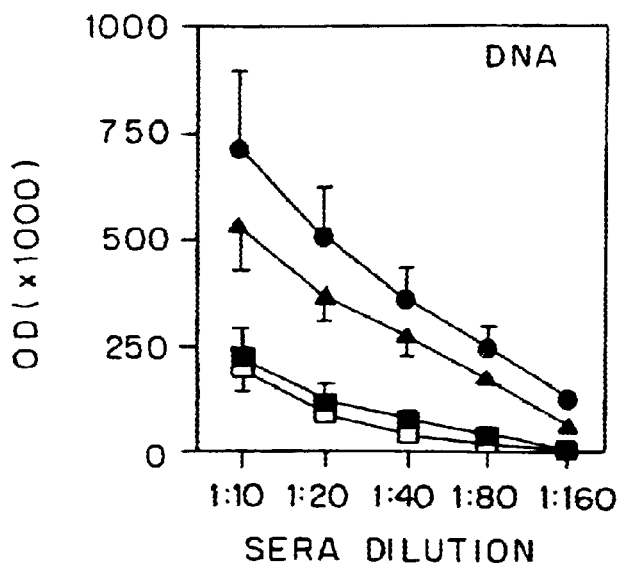
FIGS. 4A–B show the presence of anti-DNA (4A) and anti-HeLa NE (4B) antibodies in the sera of BALB/c mice tolerized with peptide Ia or with control peptide p307, and immunized with either peptide Ia or mAb 5G12.
Figure 4B:
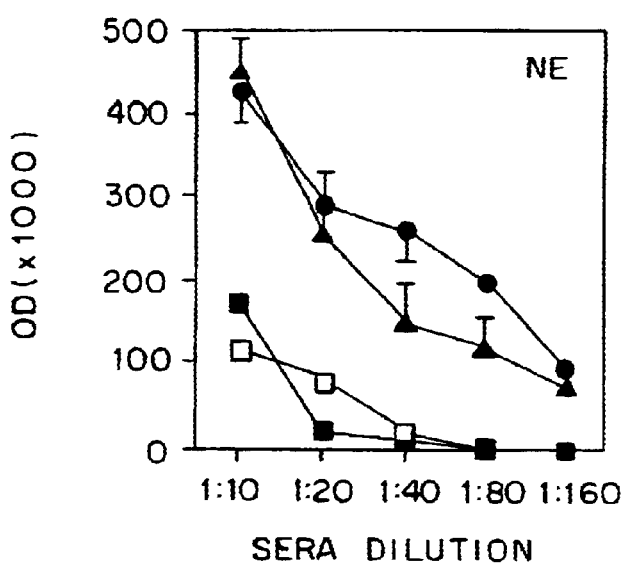

As shown in FIGS. 4A–B, BALB/c mice that were either tolerized with the peptide Ia and then immunized with the mAb 5G12 (half-filled squares), or tolerized with the peptide Ia and then immunized with the same peptide Ia (filled squares) produced lower levels of anti-DNA and anti-NE antibodies in comparison with mice that were tolerized with the non-relevant peptide p307 and then immunized with the mAb 5G12 (filled triangles), or tolerized with peptide 307 and then immunized with peptide Ia (filled circles).

This indicates that neonatal tolerization with the peptide Ia could lower the levels of autoantibodies in the sera of mice later immunized with the peptide Ia or the mAb 5G12.

Example 8
In Vivo Inhibition of Lymph Node Cell (LNC) Proliferation Responses to the CDR-based Peptides Ia and IIIa BALB/c (FIG. 5a) and SJL (FIG. 5b) mice were immunized with peptides Ia and IIIa (20 µg/mouse in CFA i.d. in the hind footpads), respectively. The mice were also injected i.v. with 200 µg of the above peptides in PBS either 3 days prior to immunization (open squares), at the immunization day (open circles) or at both dates (open triangles). Ten days later the mice were sacrificed and their lymph nodes were removed and tested for proliferation in the presence of different concentrations of the immunizing peptide. Control groups were of LNC taken from mice that were immunized but not treated (filled squares), or treated with control peptide, p307 (half filled squares). The culture mixtures were incubated for 96 hours in enriched RPMI medium containing 1% normal mouse serum prior to addition of $^3$H-thymidine. Sixteen hours later cells were harvested and radioactivity was counted. Results are expressed as mean CPM of triplicates. SD values did not exceed 10%.

Figure 5A:
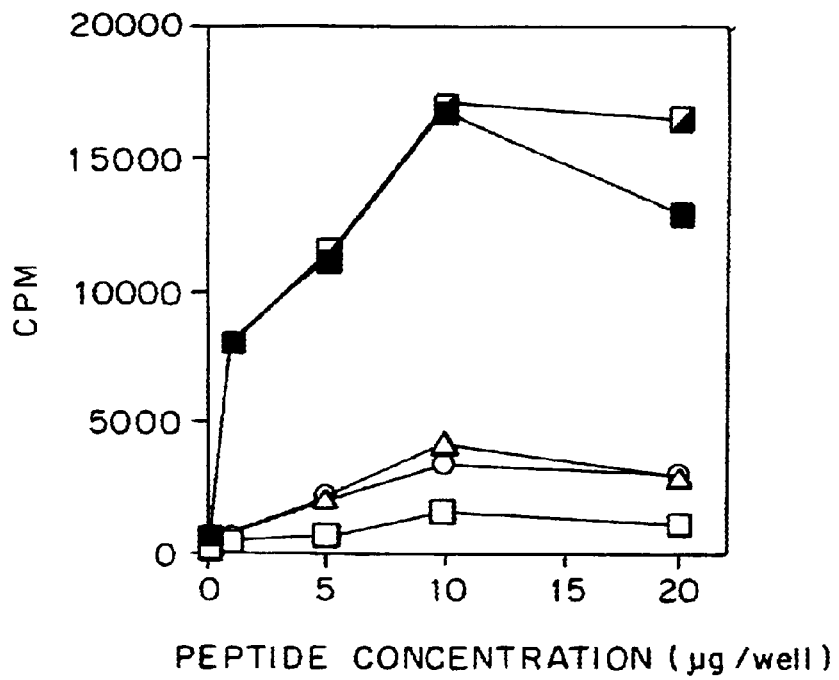
FIGS. 5a–b show in vivo inhibition of lymph node cell (LNC) proliferation responses in BALB/c (5a) and SJL (5b) mice to the CDR-based peptides Ia and IIIa, respectively, following treatment with the latter.
Figure 5B:
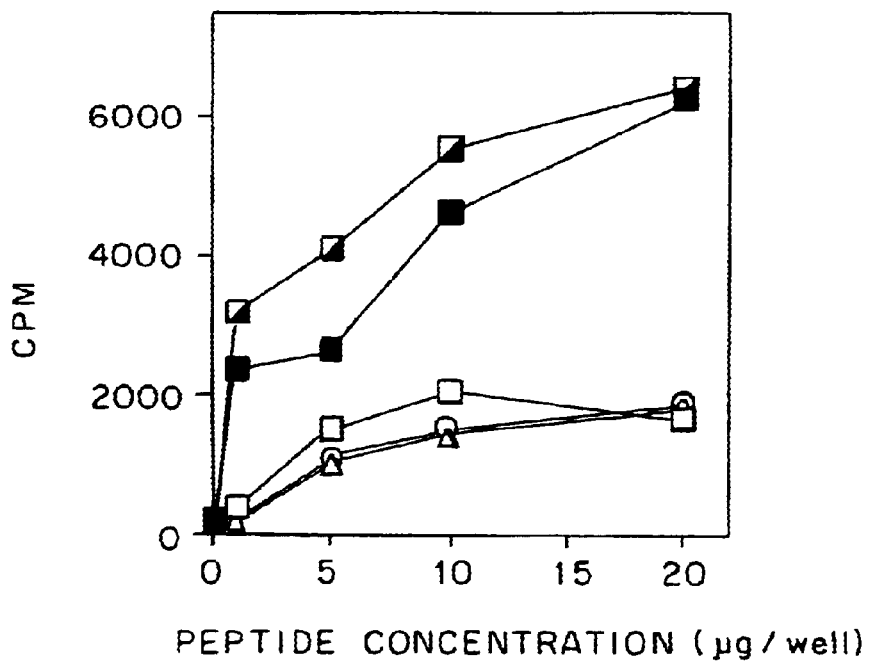

As shown in FIGS. 5a–b, both peptides Ia (5a) and IIIa (5b) inhibited proliferative responses of LNC of BALB/c and SJL mice, respectively, when injected to the mice either 3 days prior to, or at the immunization day: Up to 95% of the proliferative capacity of the cells was inhibited by the peptides. The inhibition was specific since the proliferative responses of the LNC to Con A were not inhibited by peptides Ia and IIIa (not shown).

Example 9
In Vivo Inhibition of LNC Proliferation of Mice Immunized With mAb 5G12 and Treated With Peptides Ia and IIIa.

BALB/c (FIG. 6a) and SJL (FIG. 6b) mice were immunized with mAb 5G12 (20 µg/mouse in CFA i.d. in the hind footpads) and were injected (200 µg/mouse i.v. in PBS) with either peptide Ia or IIIa, respectively. Proliferation responses to mAb 5G12 were measured in LNC taken from mice that were immunized and not treated (filled squares), treated concomitantly with immunization with the control peptide p307 (half filled squares) or treated with the appropriate CDR-based peptide Ia (6a) or IIIa (6b) (open squares). Proliferation responses to the immunodominant CDR-based peptide Ia and IIIa was also monitored in LNC taken from non-treated mice (filled circles) or from mice treated with the appropriate CDR-based peptide Ia or IIIa (open circles). Results are expressed as mean CPM of triplicates. SD values did not exceed 10%.

Figure 6A:
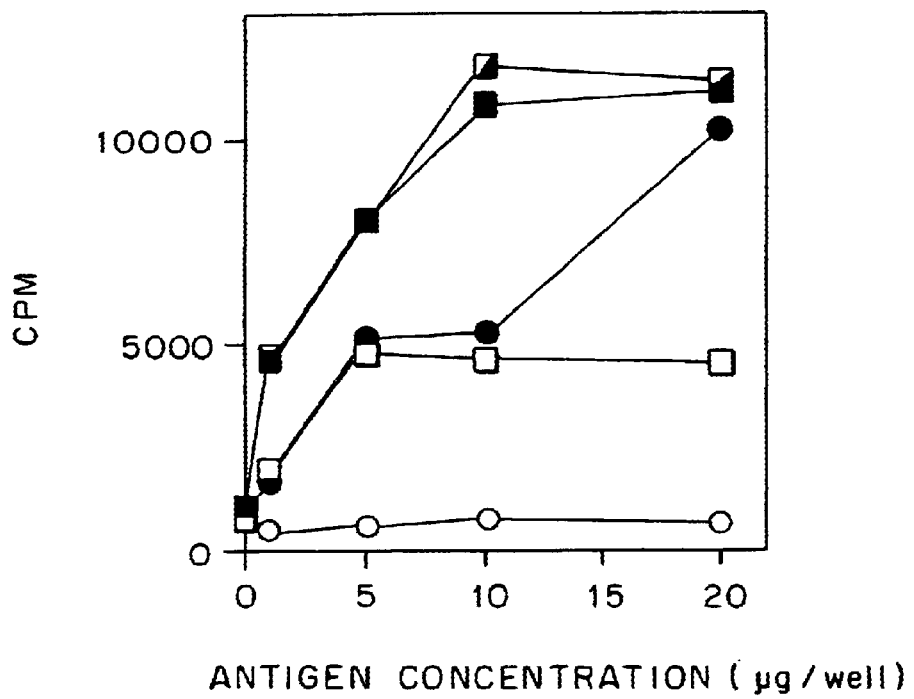
FIGS. 6a–b show in vivo inhibition of LNC to mAb 5G12 in BALB/c (6a) or SJL (6b) mice treated with peptide Ia and IIIa, respectively.
Figure 6B:
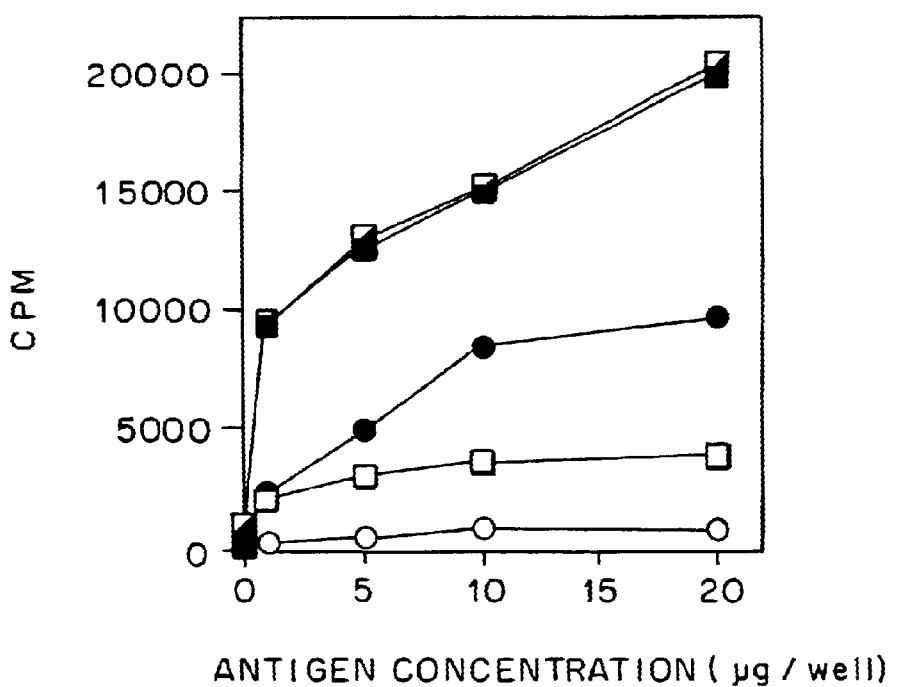

As shown in FIGS. 6a–b, proliferative responses to mAb 5G12 of LNC taken from mice treated with the appropriate CDR-based peptide were inhibited comparing to the responses of non-treated mice.

Example 10
In Vivo Inhibition of LNC Proliferation to the Human Monoclonal Anti-DNA 16/6 Id Antibody BALB/c (FIG. 7a) and SJL (FIG. 7b) mice were immunized with human mAb 16/6 Id (1 µg/mouse in CFA i.d. in the hind footpads) and were injected (200 µg/mouse i.v. in PBS) with either peptide Ia or IIIa, respectively. Proliferation responses to mAb 16/6 Id were measured in LNC taken from immunized but not-treated mice (filled squares), from mice treated concomitantly with immunization with the control peptide p307 (half filled squares) or from mice treated with the appropriate CDR-based peptide Ia or IIIa (open squares). Proliferation responses were also shown to the immunodominant CDR-based peptide Ia or IIIa of LNC taken from 16/6 Id immunized non-treated mice (filled circles) or from mice treated with the appropriate CDR-based peptide Ia or IIIa (open circles). Results are expressed as mean CPM of triplicates. SD values did not exceed 10%.

Figure 7A:
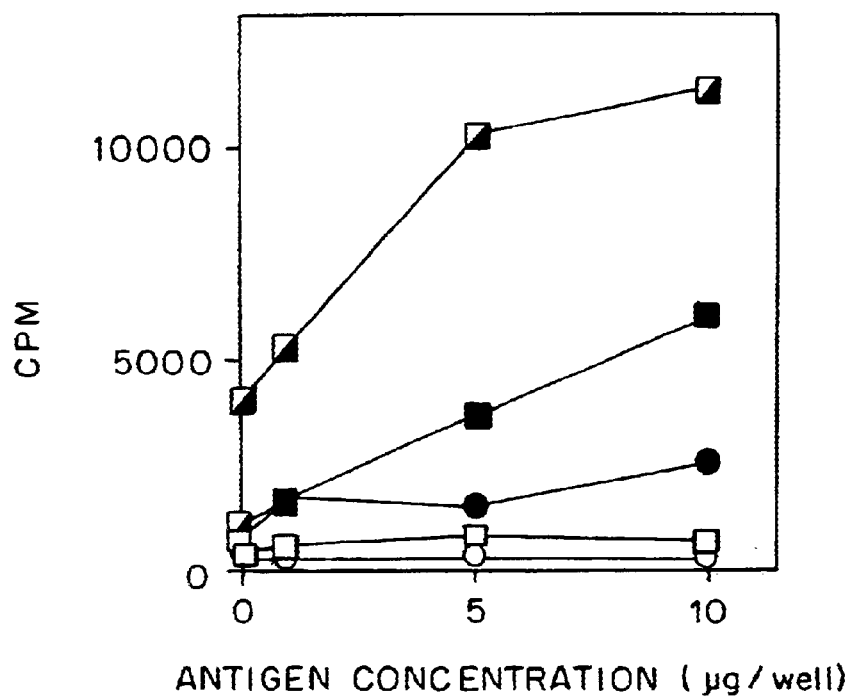
FIGS. 7a–b show in vivo inhibition of LNC proliferation to the human monoclonal anti-DNA 16/6 Id antibody in BALB/c (7a) and SJL (7b) mice treated with peptide Ia and IIa, respectively.
Figure 7B:
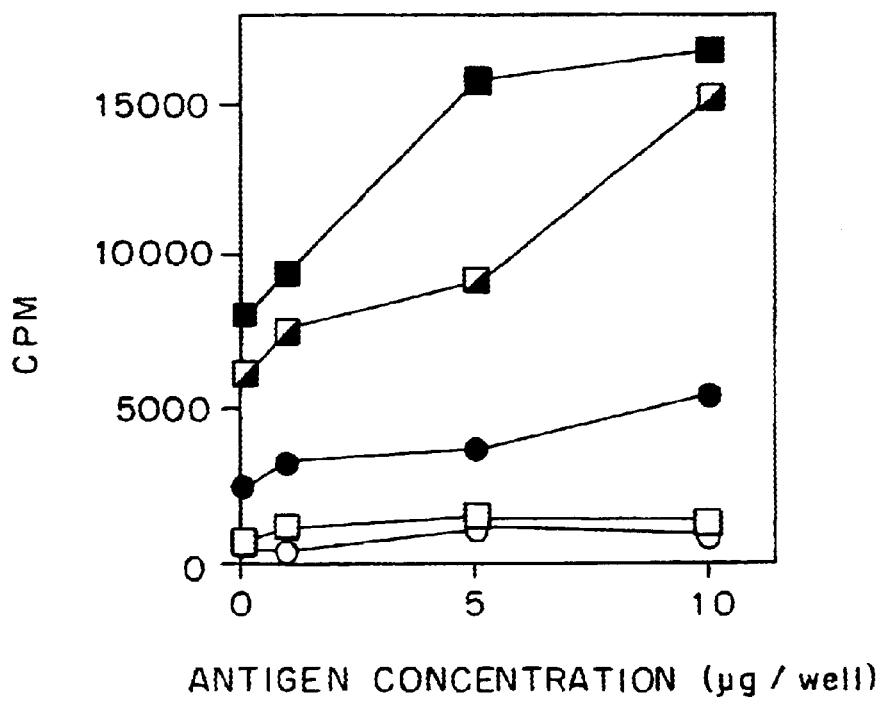
Figure 8A:
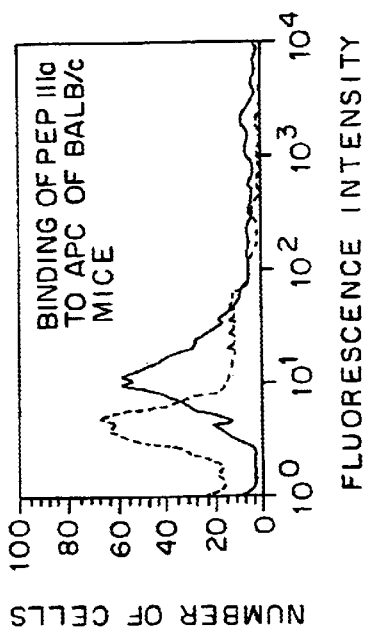
FIG. 8 shows binding of peptides Ia and IIa to the surface of splenic antigen-presenting cells of different mouse strains.
Figure 8B:
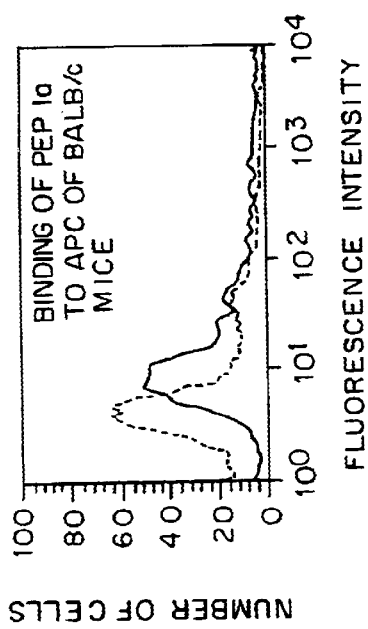
Figure 8C:
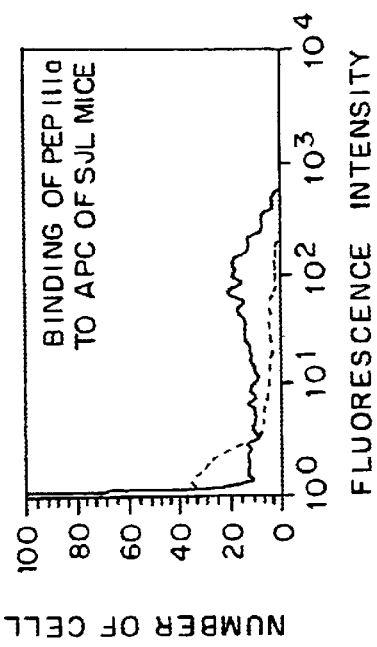
Figure 8D:
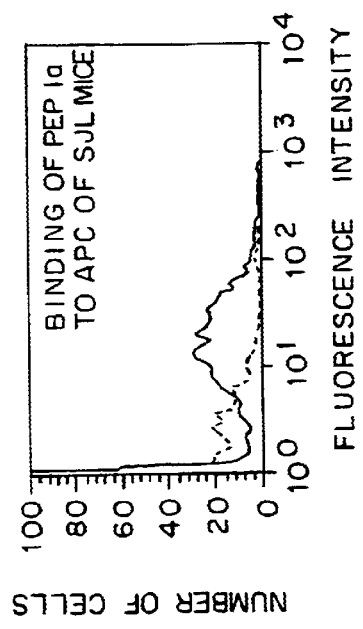
Figure 8F:
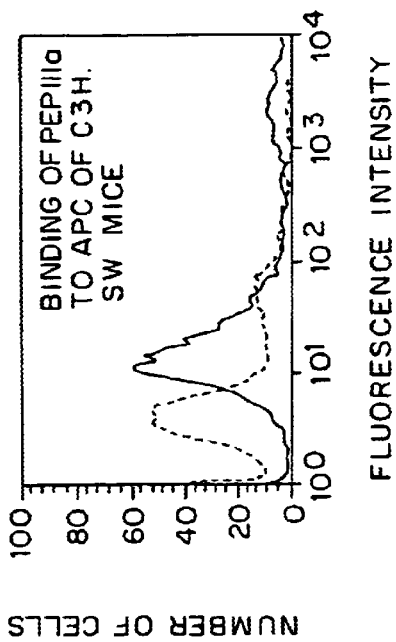
Figure 8H:
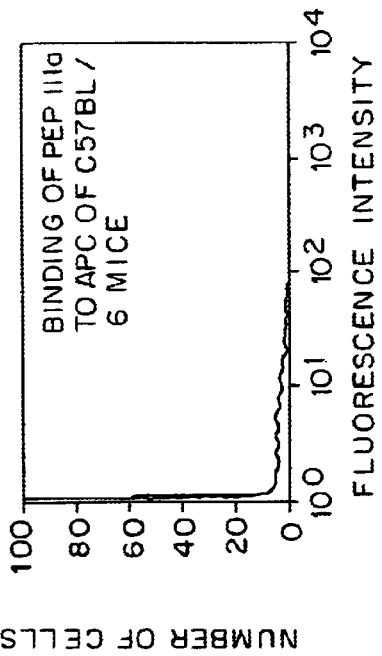
Figure 8E:
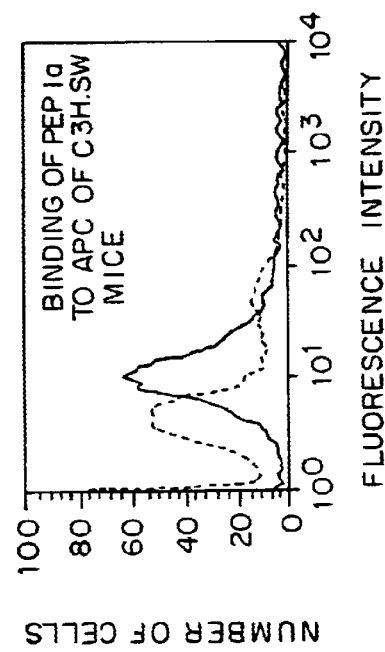
Figure 8G:
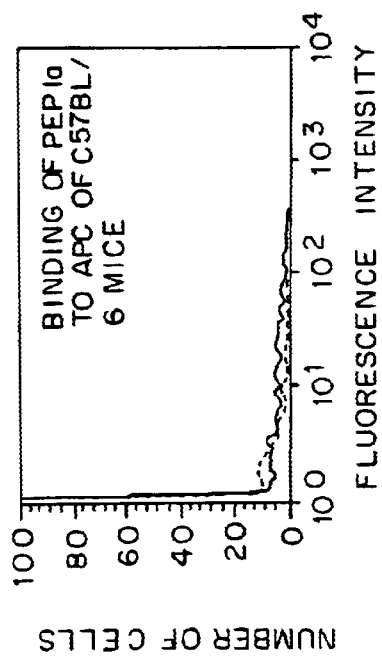

As shown in FIGS. 7a–b, proliferative responses to mAb 16/6 Id of LNC taken from mice treated with the appropriate CDR-based peptide Ia or IIIa were inhibited comparing to the responses of immunized but not treated mice, or mice treated with the control peptide p307.

Example 11
Binding of CDR-based Peptides Ia and IIIa to the Surface of Splenic Antigen-presenting Cells (APC)

Splenic adherent cells ($10^6$/100 µl/tube) isolated from BALB/c, SJL, C3H.SW or C57BL/6 mice were incubated for 16 hours with biotinylated CDR-based peptide Ia or IIIa followed by incubation with PE-streptavidin for 30 min at 4° C. Thereafter the samples were incubated with biotinylated anti-streptavidin and for an additional period with PE-streptavidin, all at 4° C. for 30 min. After washing, the cells were analysed by flow cytometry using the FACSort cytometer and CELLQuest software.

The results are shown in FIG. 8: staining of cells that were incubated with the biotinylated CDR-based peptides is marked by solid lines, and background staining with hon-biotinylated peptide is marked by broken lines. Splenic antigen-presenting cells derived from all tested mouse strains (except for C57BL/6 mice that are resistant to induction of SLE) showed significant binding of both CDR-based peptides Ia and IIIa to MHC class II products, indicating that their binding capacity agrees with the susceptibility of the mouse strains to SLE induction.

Binding of the CDR-based peptides Ia and IIIa to APC was determined as described in Materials and Methods herein and the results are shown in Table 2. Binding percentage was about 38–53% for all strains, except for APC from C57BL/6 strain which showed only 19.3% and 8.5% binding with peptides Ia and IIIa, respectively The binding was inhibited by the relevant anti-Ia antibodies showing the specificity of the binding to MHC Class II products. The results are shown in Table 3: Inhibition of binding was specific and ranged from 60% to 100%.

TABLE 2

Binding of peptides Ia and IIIa to APC of mice

| Mouse strain | H-2[a] | peptide | % binding |
|---|---|---|---|
| BALB/c | d | Ia | 45.7 |
| BALB/c | d | IIIa | 41.3 |
| SJL | s | Ia | 42.3 |
| SJL | s | IIIa | 38.0 |
| C3H.SW | b | Ia | 42.3 |
| C3H.SW | b | IIIa | 52.9 |
| C57BL/6 | b | Ia | 19.3 |
| C57BL/6 | b | IIIa | 8.5 |

[a]is the MHC Class II of the mouse

TABLE 3

Inhibition of binding of peptides Ia and IIIa to APC by anti-Ia mAb

| | | | % inhibition | |
|---|---|---|---|---|
| Mouse strain | H-2 | mAb | pep Ia | pep IIIa |
| BALB/c | d | anti I-A$^d$ (MKD6) | 76.7 | 100 |
| BALB/c | d | anti I-A$^b$ (34-5-3) | 0 | 0 |
| SJL | s | anti I-A$^s$ (10.3.6.2) | 100 | 92.8 |
| SJL | s | anti I-A$^d$ (MKD6) | 0 | 0 |

TABLE 3-continued

Inhibition of binding of peptides Ia and IIIa to APC by anti-Ia mAb

|  |  |  | % inhibition | |
|---|---|---|---|---|
| Mouse strain | H-2 | mAb | pep Ia | pep IIIa |
| C3H.SW | b | anti I-A$^b$ (34-5-3) | 60 | 84.4 |
| C3H.SW | b | anti I-A$^d$ (MKD6) | 0 | 25 |
| C57BL/6 | b | anti I-A$^b$ (34-5-3) | 82 | 59.3 |
| C57BL/6 | b | anti I-A$^d$ (MKD6) | 0 | 0 |

Example 12

Detection of Antibodies Against Peptides Ia, IIa and IIIa, and anti-16/6 Id Antibodies in the Sera of SLE Patients and Healthy Controls Human SLE patients (32 patients) were bled and their sera were tested by ELISA for their ability to bind the peptides Ia, IIa and IIIa, a control peptide p195–212 (a myasthogenic peptide described in PCT publication No. WO 94/00148) or mAb 5G12.

Detection of the antibodies was conducted on plates that were coated with 10 μg/ml of peptides Ia, IIa, IIIa or p195–212 or mAb 5G12, in PBS for 2 hr, washed and blocked with 1% ovalbumin in PBS for an additional 2 hr. ELISA was continued as described after blockage in Example 2 above, using goat anti-human IgG polyclonal antibody conjugated to peroxidase.

Figure 9:
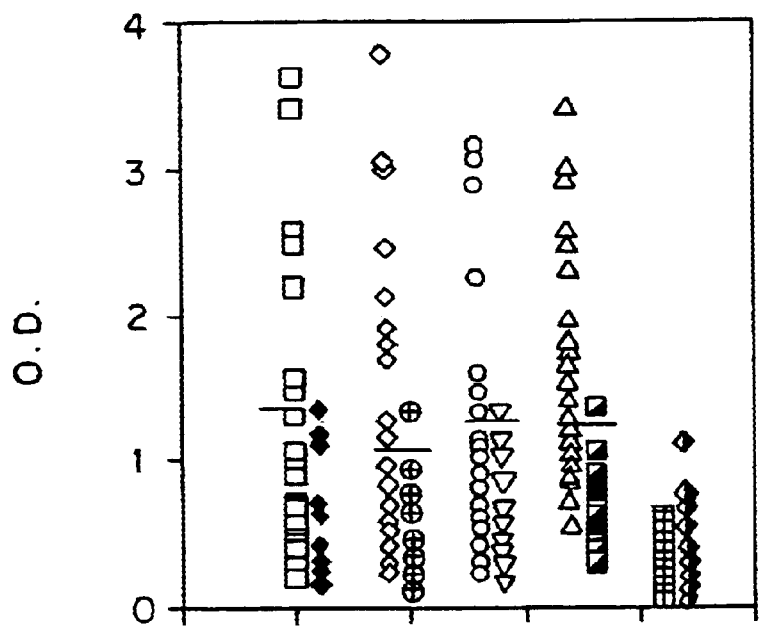
FIG. 9 shows antibody titers in sera of SLE patients and healthy human controls by testing their sera for the ability to bind the peptides Ia, IIa and IIIa, or mAb 5G12 or a control peptide.

As shown in FIG. 9, SLE patients exhibited significantly higher levels of antibodies that bind either peptide Ia (open squares), IIa (open diamonds) or IIIa (open circles), or mAb 5G12 (open triangles), in comparison to healthy controls (peptide Ia-healthy—closed diamonds; peptide IIa-healthy—crossed circles; peptide IIIa-healthy—inverted open triangles; 5G12-healthy—half filled squares). No binding could be observed when either sera of patients or controls were tested on plates coated with the non-relevant peptide p195–212 (p195–212-SLE—crossed squares; p195–212-healthy—half filled diamonds). The results indicate a correlation between the whole antibody molecule and the CDR-based peptides on the level of antibody titers.

Example 13

Proliferation of PBL From SLE Patients and Healthy Controls in the Presence of Human 16/6 Id mAb and Peptides Peripheral blood lymphocytes (PBL) were isolated from the blood of SLE patients or healthy controls using ficol gradient. Thereafter, the PBL were incubated in the presence of different concentrations of the peptides Ia, IIa or IIIa, or the human 16/6 Id mAb for 24 hr, when a sample was taken for IL-2 measurement. The assay was continued for a total of 7 days, and $^3$H-thymidine was added for the last 16 hr. Proliferation was detected by reading the amount of radioactivity incorporated into the DNA of the cells.

As is seen in Table 4, a lower proportion of the PBL taken from SLE patients reacted to the peptides or to the 16/6 Id mAb, when compared to the healthy controls. The results are expressed in percentage of responder (34% in the first line) and the actual number of patients (11 out of 32:11/32)

Similar results were obtained when the levels of the IL-2 produced by the PBL in the presence of the peptides or the 16/6 Id mAb were tested, as shown in the next example.

TABLE 4

Proliferation of PBL from SLE Patients and Healthy Controls in Presence of mAb 16/6 Id and Peptides Ia-IIIa

|  | SLE Patients | | Healthy Controls | |
|---|---|---|---|---|
| 16/6 Id | 34% | 11/32 | 72% | 18/25 |
| pep Ia | 21% | 7/32 | 44% | 11/25 |
| pep IIa | 9% | 3/32 | 28% | 7/25 |
| pep IIIa | 31% | 10/32 | 60% | 15/25 |

Example 14

Production of IL-2 by PBL of SLE Patients and Healthy Controls in the Presence of Human mAb 1616 Id and Peptides PBL were isolated from blood of SLE patients or healthy controls using ficol gradient, and were incubated as in Example 13. A sample of 50 μl was removed 24 hr after the assay was started, and incubated in the presence of IL-2 sensitive cells (CTLD) for 24 hr, after which $^3$H-thymidine was added for 16 hr, and the plates were harvested and counted on a beta counter.

As in Table 4, it can also be seen from Table 5 that a lower proportion of the PBL taken from SLE patients reacted to the peptides or to the 1616 Id mAb, when compared to the healthy controls, thus indicating that the response to the peptide corresponds to that of T cells of the patient to the pathogenic human autoantibody.

TABLE 5

IL-2 Production by PBL of SLE Patients and Healthy Controls in Presence of mAb 16/6 Id and Peptides Ia-IIIa

|  | SLE Patients | | Healthy Controls | |
|---|---|---|---|---|
| 16/6 Id | 31% | 10/32 | 66% | 17/25 |
| pep Ia | 16% | 5/32 | 56% | 14/25 |
| pep IIa | 9% | 3/32 | 32% | 8/25 |
| pep IIIa | 16% | 5/32 | 64% | 16/25 |

REFERENCES

1. Axelrod, O. and Mozes, E. *Immunobiology* 172: 99, 1986.
2. Conlon, P. J. *J. Immunol.* 134: 1280, 1983.
3. Fricke, H., Offen, D., Mendlovic, S., Shoenfeld, Y., Bakimer, R., Sperling, J. and Mozes, E. *Internatl. Immunol.* 2: 225, 1990.
4. Fricke, H., Mendlovic, S., Blank, M., Shoenfeld, Y., Ben-Bassat, M. and Mozes, E. *Immunology* 73: 421, 1991.
5. Mendlovic, S., Brocke, S., Shoenfeld, Y., Ben-Bassat, M., Meshorer, A., Bakimer, R. and Mozes, E. E. *Proc. Natl. Acad. Sci. USA* 85: 2260, 1988.
6. Mendlovic, S., Fricke, H., Shoenfeld, Y. and Mozes E. *Eur. J. Immunol.* 19: 729, 1989.
7. Mendlovic, S., Brocke, S., Fricke, H., Shoenfeld, Y., Bakimer, R. and Mozes, E. *Immunology* 69: 228, 1990.
8. Mozes, E., Dayan, M., Zisman, E., Brocke, S., Licht, A. and Pecht, I. *EMBO J.* 8: 4049, 1989.
9. Ruiz, P. J., Zinger, H. and Mozes, E. *Immunol. Lett.* 41: 79, 1994.
10. Shoenfeld, Y., Isenberg, D. A., Rauch, J., Madaio, M. P., Stollar, B. D. and Schwartz, R.S. *J. Exp. Med.* 158: 718, 1983.

11. Sthoeger, Z. M., Tartakovsky, B., Bentwich, Z. and Mozes, E. *J. Clin. Immumol.* 13: 127, 1993.
12. Waisman, A., Mendlovic, S., Ruiz, P. J., Zinger, H., Meshorer, A. and Mozes, E. *Internal. Immunol.* 5: 1293, 1993.
13. Waisman, A. and Mozes, E. *Eur. J. Immunol.* 23:1566, 1993.
14. Zisman, E., Sela, M. and Mozes. E. *Proc. Natl. Acad. Sci. USA* 88: 9738, 1991.
15. Zamvil et al., *J. Exp. Med.* 167: 1586, 1988.

What is claimed is:

1. A synthetic peptide selected from the group consisting of:
   (i) a peptide of at least 12 and at most 30 amino acid residues consisting of a sequence including a complementarity-determining region found in the heavy or light chain of a pathogenic anti-DNA monoclonal antibody that induces a systemic lupus erythematosus (SLE)-like disease in mice, or a salt thereof or the reaction product thereof with an organic derivatizing agent capable of reacting with selected side chains or terminal residues, which reaction product retains at least a portion of the function of the peptide to inhibit specifically the proliferative response and cytokine secretion of T lymphocytes of mice that are high responders to SLE-inducing autoantibodies;
   (ii) a dual synthetic peptide comprising two different ones of said peptides of (i) covalently linked to one another either directly or through a short linking chain;
   (iii) a peptide polymer comprising a plurality of sequences of said peptide (i); and
   (iv) a peptide polymer of (iii) attached to a macromolecular carrier.

2. A synthetic peptide according to claim 1, capable of:
   (i) inhibiting specifically the proliferative response and cytokine secretion of T lymphocytes of mice that are high responders to SLE-inducing autoantibodies; or
   (ii) inhibiting development of SLE in mice that are susceptible to SLE-induction by pathogenic autoantibodies.

3. A pharmaceutical composition comprising a synthetic peptide or peptide polymer according to claim 1, and a pharmaceutically acceptable carrier.

4. A method of selecting peptides capable of inhibiting the proliferative response of T lymphocytes from a systemic lupus erythematosus (SLE) patient, comprising:
   (i) synthesizing a peptide of at least 12 and at most 30 amino acid residues consisting of a sequence including a complementarity-determining region found in the heavy or light chain of a pathogenic anti-DNA monoclonal antibody that induces a SLE-like disease in mice, or an analog of said peptide;
   (ii) testing said peptide or analog for its ability to inhibit the proliferative response of T cells from a SLE patient, or a T cell line or clone which is specific to the 16/6 Id anti-DNA monoclonal antibody to which the T cells are specific; and
   (iii) selecting and producing additional quantities of said peptide only if it is capable of inhibiting said proliferative response.

5. A synthetic peptide selected from the group consisting of:
   (i) a peptide consisting of the sequence of SEQ ID NO:1, 2, 3, 4 or 5;
   (ii) a dual synthetic peptide comprising two different ones of said peptides of (i) covalently linked to one another either directly or through a short linking chain;
   (iii) a peptide polymer comprising a plurality of sequences of said peptide (i); and
   (iv) a peptide polymer of (iii) attached to a macromolecular carrier.

6. A synthetic peptide according to claim 5, capable of:
   (i) inhibiting specifically the proliferative response and cytokine secretion of T lymphocytes of mice that are high responders to SLE-inducing autoantibodies; or
   (ii) inhibiting development of SLE in mice that are susceptible to SLE-induction by pathogenic autoantibodies.

7. A synthetic peptide according to claim 5, consisting of the sequence of SEQ ID NO:6.

8. A synthetic peptide according to claim 5, consisting of the sequence of SEQ ID NO:7.

9. A synthetic peptide according to claim 5, consisting of the sequence of SEQ ID NO:8.

10. A synthetic peptide according to claim 5, consisting of the sequence of SEQ ID NO:9.

11. A synthetic peptide according to claim 5, consisting of the sequence of SEQ ID NO:10.

12. A synthetic peptide according to claim 1, comprising a dual synthetic peptide of (ii).

13. A synthetic peptide according to claim 5, comprising a dual synthetic peptide of (ii).

14. A dual synthetic peptide of claim 12, wherein said two peptides are linked covalently.

15. A dual synthetic peptide of claim 13, wherein said two peptides are linked covalently.

16. A synthetic peptide according to claim 1, comprising a peptide polymer of (iii).

17. A synthetic peptide according to claim 5, comprising a peptide polymer of (iii).

18. A synthetic peptide according to claim 5, wherein the peptide of (i) consists of the sequence of SEQ ID NO:1.

19. A pharmaceutical composition comprising a synthetic peptide or peptide polymer according to claim 5, and a pharmaceutically acceptable carrier.

20. A pharmaceutical composition comprising a mixture of at least two different peptides from those peptides as defined in claim 5 (i).

21. A synthetic peptide in accordance with claim 1, wherein said peptide of (i) is one bearing the 16/6 idiotype.

22. A synthetic peptide selected from the group consisting of:
   (i) a peptide of at least 12 and at most 30 amino acid residues consisting of a sequence including a complementarity-determining region found in the heavy or light chain of a pathogenic anti-DNA monoclonal antibody that induces a systemic lupus erythematosus (SLE)-like disease in mice, or a salt thereof or the reaction product thereof with an organic derivatizing agent capable of reacting with selected side chains or terminal residues, which reaction product retains at least a portion of the function of the peptide to inhibit development of SLE in mice that are susceptible to SLE-induction by pathogenic autoantibodies;
   (ii) a dual synthetic peptide comprising two different ones of said peptides of (i) covalently linked to one another either directly or through a short linking chain;
   (iii) a peptide polymer comprising a plurality of sequences of said peptide (i); and
   (iv) a peptide polymer of (iii) attached to a macromolecular carrier.

23. A pharmaceutical composition comprising a synthetic peptide or peptide polymer according to claim 22, and a pharmaceutically acceptable carrier.

24. A synthetic peptide according to claim 22, comprising a dual synthetic peptide of (ii).

25. A dual synthetic peptide of claim 24, wherein said two peptides are linked covalently.

26. A synthetic peptide according to claim 22, comprising a peptide polymer of (iii).

27. A synthetic peptide in accordance with claim 22, wherein said peptide of (i) is one bearing the 16/6 idiotype.

28. A method for testing peptides for their capability of inhibiting the proliferative response of T lymphocytes from a systemic lupus erythematosus (SLE) patient, comprising:

(i) synthesizing peptides of at least 12 and at most 30 amino acids consisting of a sequence including a complementarity-determining region found in the heavy or light chain of a pathogenic anti-DNA monoclonal antibody that induces a SLE-like disease in mice;

(ii) testing said peptides for their ability to inhibit the proliferative response of T cells from a SLE patient, or a T cell line or clone which is specific to the 16/6 Id anti-DNA monoclonal antibody to which the T cells are specific; and (iii) selecting the peptides shown to be capable of inhibiting said proliferative response.

* * * * *

UNITED STATES PATENT AND TRADEMARK OFFICE
CERTIFICATE OF CORRECTION

PATENT NO. : 6,613,536 B1
DATED : September 2, 2003
INVENTOR(S) : Edna Mozes and Ari Waisman It is certified that error appears in the above-identified patent and that said Letters Patent is hereby corrected as shown below:

Column 1,
Line 26, delete "pro(ducts" and insert therefor -- products --

Column 6,
Lines 43-45, delete in entirety and insert therefor

```
--1  2  3  4  5  6  7  8  9  10 11 12 13 14 15 16 17 18 19 20
   T  G  Y  Y  M  Q  W  V  K  Q     S     P  E  K  S  L  E  W  I  G
     (SEQ ID NO:6)                                              (Ia)--
```

Lines 54-56, delete in entirety and insert therefor

```
--1  2  3  4  5  6  7  8  9  10 11 12 13 14 15 16 17 18 19 20
   E  I  N  P  S  Y  G  G  T  T     Y     N  Q  K  F  K  A  K  A  T
     (SEQ ID NO:7)                                             (IIa)--
```

Lines 65-67, delete in entirety and insert therefor

```
--1  2  3  4  5  6  7  8  9  10 11 12 13 14 15 16 17 18 19 20
   Y  Y  C  A  R  F  L  W  E  P     A     A  M  D  Y  W  G  Q  G  S
     (SEQ ID NO:8)                                            (IIIa)--
```

Column 7,
Lines 9-11, delete in entirety and insert therefor

```
--1  2  3  4  5  6  7  8  9  10 11 12 13 14 15 16 17 18 19
   G  Y  N  M  N  W  V  K  Q  S     H     G  K  S  L  E  W  I  6
     (SEQ ID NO:9)                                             (IVa)--
```

Lines 20-21, delete in entirety and insert therefor

```
--1  2  3  4  5  6  7  8  9  10 11 12 13 14 15 16 17 18
   Y  Y  C  A  R  S  G  R  Y  G     N     Y  W  G  Q  G  T  L
     (SEQ ID NO:10)                                            (Va)--
```

Column 8,
Line 6, delete "oh" and insert therefor -- or --
Lines 34 and 35, delete "it7" and insert therefor -- in --
Line 66, delete "iii" and insert therefor -- in --

Column 15,
Line 33, delete "of" and insert therefor -- or --
Line 34, delete "IIa" and insert therefor -- IIIa --
Line 37, delete "IIa" and insert therefor -- IIIa -- and delete "anf" and insert therefor -- and --

UNITED STATES PATENT AND TRADEMARK OFFICE
CERTIFICATE OF CORRECTION

PATENT NO. : 6,613,536 B1
DATED : September 2, 2003
INVENTOR(S) : Edna Mozes and Ari Waisman It is certified that error appears in the above-identified patent and that said Letters Patent is hereby corrected as shown below:

Column 15 (cont'd),
Lines 42 and 66, delete "IIa" and insert therefor -- IIIa --

Signed and Sealed this

Seventh Day of September, 2004

JON W. DUDAS
*Director of the United States Patent and Trademark Office*

```
                          SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION:/note= Xaa in position 5 is Met, Ala or
            Val; Xaa in position 6 is Gln, Asp, Glu, or Arg; Xaa in
            position 7 is Trp or Ala; Xaa in position 8 is Val or Ser;and
            Xaa in position 9 is Lys, Glu or Ala.

(xi) SEQUENCE DESCRIPTION: SEQ ID NO: 1:

Thr Gly Tyr Tyr Xaa Xaa Xaa Xaa Xaa Gln Ser Pro Glu Lys Ser Leu
1               5                   10                  15

Glu Trp Ile Gly
            20

(2) INFORMATION FOR SEQ ID NO: 2:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION:/note= Xaa in position 9 is Thr, Val or
            Ala; Xaa in position 10 is Thr, Val or Ala; Xaa in position 11
            is Tyr or Phe; Xaa in position 12 is Asn or Asp; Xaa in
            position 13 is Gln or Glu; Xaa in position 14 is Lys or Glu;
            and Xaa in position 15 is Phe or Tyr.

(xi) SEQUENCE DESCRIPTION: SEQ ID NO: 2:

Glu Ile Asn Pro Ser Thr Gly Gly Xaa Xaa Xaa Xaa Xaa Xaa Xaa Lys
1               5                   10                  15

Ala Lys Ala Thr
            20

(2) INFORMATION FOR SEQ ID NO: 3:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION:/note= Xaa in position 6 is Phe, Thr or
            Gly; Xaa in position 7 is Leu, Ala or Ser; Xaa in position 8
``` is Trp or Ala; Xaa in position 9 is Glu or Lys; Xaa in
position 13 is Met or Ala; and Xaa in position 14 is Asp, Lys
or Ser.

(xi) SEQUENCE DESCRIPTION: SEQ ID NO: 3:

Tyr Tyr Cys Ala Arg Xaa Xaa Xaa Xaa Pro Tyr Ala Xaa Xaa Tyr Trp
1               5                   10                  15

Gly Gln Gly Ser
        20

(2) INFORMATION FOR SEQ ID NO: 4:

(i) SEQUENCE CHARACTERISTICS:
       (A) LENGTH: 19 amino acids
       (B) TYPE: amino acid
       (C) STRANDEDNESS: single
       (D) TOPOLOGY: linear (ii) MOLECULE TYPE: peptide (ix) FEATURE:
       (D) OTHER INFORMATION:/note= Xaa in position 4 is Met or Ala;
       Xaa in position 5 is Asn, Asp or Arg; Xaa in position 6 is
       Trp or Ala; Xaa in position 7 is Val or Ser; Xaa in position 8
       is Lys or Glu; Xaa in position 9 is Gln or Ala; Xaa in
       position 13 is Lys or Glu; and Xaa in position 14 is Ser or
       Ala.

(xi) SEQUENCE DESCRIPTION: SEQ ID NO: 4:

Gly Tyr Asn Xaa Xaa Xaa Xaa Xaa Xaa Ser His Gly Xaa Xaa Leu Glu
1               5                   10                  15

Trp Ile Gly (2) INFORMATION FOR SEQ ID NO: 5:

(i) SEQUENCE CHARACTERISTICS:
       (A) LENGTH: 18 amino acids
       (B) TYPE: amino acid
       (C) STRANDEDNESS: single
       (D) TOPOLOGY: linear (ii) MOLECULE TYPE: peptide (ix) FEATURE:
       (D) OTHER INFORMATION:/note= Xaa in position 6 is Ser or Phe;
       Xaa in position 7 is Gly or Ala; Xaa in position 8 is Arg, Ala
       or Glu; Xaa in position 11 is Asn or Asp; Xaa in position 12
       is Tyr or Phe; and Xaa in position 13 is Trp, His or Ala.

(xi) SEQUENCE DESCRIPTION: SEQ ID NO: 5:

Tyr Tyr Cys Ala Arg Xaa Xaa Xaa Tyr Gly Xaa Xaa Xaa Gly Gln Gly
1               5                   10                  15

Thr Leu (2) INFORMATION FOR SEQ ID NO: 6:

(i) SEQUENCE CHARACTERISTICS:
       (A) LENGTH: 20 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 6:

Thr Gly Tyr Tyr Met Gln Trp Val Lys Gln Ser Pro Glu Lys Ser Leu
1               5                   10                  15

Glu Trp Ile Gly (2) INFORMATION FOR SEQ ID NO: 7:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

Glu Ile Asn Pro Ser Thr Gly Gly Thr Thr Tyr Asn Gln Lys Phe Lys
1               5                   10                  15

Ala Lys Ala Thr
            20

(2) INFORMATION FOR SEQ ID NO: 8:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

Tyr Tyr Cys Ala Arg Phe Leu Trp Glu Pro Tyr Ala Met Asp Tyr Trp
1               5                   10                  15

Gly Gln Gly Ser
            20

(2) INFORMATION FOR SEQ ID NO: 9:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

Gly Tyr Asn Met Asn Trp Val Lys Gln Ser His Gly Lys Ser Leu Glu
1               5                   10                  15

Trp Ile Gly (2) INFORMATION FOR SEQ ID NO: 10:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

Tyr Tyr Cys Ala Arg Ser Gly Arg Tyr Gly Asn Tyr Trp Gly Gln Gly
1               5                   10                  15

Thr Leu